US011213568B2

(12) United States Patent
Wang et al.

(10) Patent No.: US 11,213,568 B2
(45) Date of Patent: Jan. 4, 2022

(54) NERVE GROWTH FACTOR MUTANT

(71) Applicant: Staidson (Beijing) Biopharmaceuticals Co., Ltd., Beijing (CN)

(72) Inventors: Chao Wang, Beijing (CN); Lei Ma, Beijing (CN); Tianfei Du, Beijing (CN)

(73) Assignee: Staidson (Beijing) Biopharmaceuticals Co., Ltd., Beijing (CN)

(*) Notice: Subject to any disclaimer, the term of this patent is extended or adjusted under 35 U.S.C. 154(b) by 16 days.

(21) Appl. No.: 16/085,977

(22) PCT Filed: Mar. 17, 2017

(86) PCT No.: PCT/CN2017/077038
§ 371 (c)(1),
(2) Date: Sep. 17, 2018

(87) PCT Pub. No.: WO2017/157326
PCT Pub. Date: Sep. 21, 2017

(65) Prior Publication Data
US 2019/0105373 A1 Apr. 11, 2019

(30) Foreign Application Priority Data

Mar. 18, 2016 (CN) .......................... 201610159303.7

(51) Int. Cl.
| | |
|---|---|
| *C07K 14/48* | (2006.01) |
| *A61K 38/18* | (2006.01) |
| *C12N 15/85* | (2006.01) |
| *A61P 25/00* | (2006.01) |
| *A61K 38/00* | (2006.01) |

(52) U.S. Cl.
CPC ............ *A61K 38/18* (2013.01); *A61K 38/185* (2013.01); *A61P 25/00* (2018.01); *C07K 14/48* (2013.01); *C12N 15/85* (2013.01); *A61K 38/00* (2013.01); *C07K 2319/30* (2013.01)

(58) Field of Classification Search
CPC .................................................... C07K 14/48
See application file for complete search history.

(56) References Cited

U.S. PATENT DOCUMENTS

| | | | |
|---|---|---|---|
| 5,349,055 | A | 9/1994 | Persson et al. |
| 7,452,863 | B1 | 11/2008 | Presta et al. |
| 7,935,671 | B2 | 5/2011 | Urfer et al. |
| 8,101,571 | B2 | 1/2012 | Presta et al. |
| 2012/0230990 | A1 | 9/2012 | Beckmann et al. |

FOREIGN PATENT DOCUMENTS

| | | |
|---|---|---|
| CN | 1079992 A | 12/1993 |
| CN | 1698883 A | 11/2005 |
| CN | 102665759 A | 9/2012 |
| CN | 103159843 A | 6/2013 |
| CN | 105273087 A | 1/2016 |
| WO | WO 2008/006893 A1 | 1/2008 |
| WO | WO 2009/080823 A2 | 7/2009 |

OTHER PUBLICATIONS

Capsoni, Simona et al., "Taking Pain Out of NGF: A "Painless" NGF Mutant, Linked to Hereditary Sensory Autonomic Neuropathy Type V, with Full Neurotrophic Activity" PLoS ONE, Feb. 2011, pp. 1-12, vol. 6, Issue 2, e17321.
Niranjana, K.R.P. et al., "Fc IgG1 heavy chain constant region, partial [*Homo sapiens*]" GenBank Accession ID: AEV43323. 1, Dec. 11, 2011.
Urfer, Roman et al., "The binding epitopes of neurotrophin-3 to its receptors trkC and gp75 and the design of a multifunctional human neurotrophin" The EMBO Journal, 1994, pp. 5896-5909, vol. 13, No. 24.
Wiesmann, C. et al., "Nerve growth factor: structure and function" CMLS, Cellular and Molecular Life Sciences, 2001, pp. 748-759, vol. 58.
International Search Report for PCT/CN2017/077038 dated Jun. 15, 2017.
Written Opinion for PCT/CN2017/077038 dated Jun. 15, 2017.
Fukui, Yu et al., "Low Affinity NGF Receptor (p75 Neurotrophin Receptor) Inhibitory Antibody Reduces Pain Behavior and CGRP Expression in DRG in the Mouse Sciatic Nerve Crush Model" Journal of Orthopaedic Research, Mar. 2010, pp. 279-283.
Rydén, Mikael et al., "A Second Determinant of Binding to the p75 Neurotrophin Receptor Revealed by Alanine-scanning Mutagenesis of a Conserved Loop in Nerve Growth Factor" The Journal of Biological Chemistry, Dec. 1997, pp. 33085-33091, vol. 272, No. 52.
Supplementary European Search Report for EP 17765867 dated Jul. 4, 2019.
Supplementary Partial European Search Report for EP 17765868 dated Aug. 9, 2019.

*Primary Examiner* — Robert C Hayes
(74) *Attorney, Agent, or Firm* — Knobbe Martens Olson & Bear LLP

(57) ABSTRACT

Provided is a nerve growth factor mutant, wherein same is an amino acid sequence as shown by any one of SEQ ID No: 3 to SEQ ID No: 21 in the sequence listing. The advantage of the nerve growth factor mutant lies in that the mutation of a nerve growth factor can alleviate side effects such as pain, falling within the field of biological pharmacy.

9 Claims, 5 Drawing Sheets
Specification includes a Sequence Listing.

SEQUENCE LISTING

```
<160> NUMBER OF SEQ ID NOS: 42

<210> SEQ ID NO 1
<211> LENGTH: 726
<212> TYPE: DNA
<213> ORGANISM: Homo sapiens

<400> SEQUENCE: 1
atgtccatgt tgttctacac tctgatcaca gcttttctga tcggcataca ggcggaacca      60
cactcagaga gcaatgtccc tgcaggacac accatccccc aagcccactg gactaaactt     120
cagcattccc ttgacactgc ccttcgcaga gcccgcagcg ccccggcagc ggcgatagct     180
gcacgcgtgg cggggcagac ccgcaacatt actgtggacc ccaggctgtt taaaaagcgg     240
cgactccgtt caccccgtgt gctgtttagc acccagcctc cccgtgaagc tgcagacact     300
caggatctgg acttcgaggt cggtggtgct gccccttca acaggactca caggagcaag     360
cggtcatcat cccatcccat cttccacagg ggcgaattct cggtgtgtga cagtgtcagc     420
gtgtgggttg gggataagac caccgccaca gacatcaagg gcaaggaggt gatggtgttg     480
ggagaggtga acattaacaa cagtgtattc aaacagtact tttttgagac caagtgccgg     540
gacccaaatc ccgttgacag cgggtgccgg ggcattgact caaagcactg gaactcatat     600
tgtaccacga ctcacacctt tgtcaaggcg ctgaccatgg atggcaagca ggctgcctgg     660
cggtttatcc ggatagatac ggcctgtgtg tgtgtgctca gcaggaaggc tgtgagaaga     720
gcctga                                                                726

<210> SEQ ID NO 2
<211> LENGTH: 120
<212> TYPE: PRT
<213> ORGANISM: Homo sapiens

<400> SEQUENCE: 2

Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Lys
            20                  25                  30

Gly Lys Glu Val Met Val Leu Gly Glu Val Asn Ile Asn Asn Ser Val
        35                  40                  45

Phe Lys Gln Tyr Phe Phe Glu Thr Lys Cys Arg Asp Pro Asn Pro Val
    50                  55                  60

Asp Ser Gly Cys Arg Gly Ile Asp Ser Lys His Trp Asn Ser Tyr Cys
65                  70                  75                  80
```

```
Thr Thr Thr His Thr Phe Val Lys Ala Leu Thr Met Asp Gly Lys Gln
            85                  90                  95

Ala Ala Trp Arg Phe Ile Arg Ile Asp Thr Ala Cys Val Cys Val Leu
            100                 105                 110

Ser Arg Lys Ala Val Arg Ala
            115                 120

<210> SEQ ID NO 3
<211> LENGTH: 120
<212> TYPE: PRT
<213> ORGANISM: Homo sapiens

<400> SEQUENCE: 3

Ser Ser Ser His Pro Ile Phe His Arg Gly Glu Ser Val Cys Asp
1               5                   10                  15

Ser Val Ser Val Trp Val Gly Asp Lys Thr Thr Ala Thr Asp Ile Lys
            20                  25                  30

Gly Lys Glu Val Met Val Leu Gly Glu Val Asn Ile Asn Asn Ser Val
            35                  40                  45

Phe Lys Gln Tyr Phe Phe Glu Thr Lys Cys Arg Asp Pro Asn Pro Val
    50                  55                  60

Asp Ser Gly Cys Arg Gly Ile Asp Ser Lys His Trp Asn Ser Tyr Cys
65                  70                  75                  80

Thr Thr Thr His Thr Phe Val Lys Ala Leu Thr Met Asp Gly Lys Gln
            85                  90                  95

Ala Ala Trp Arg Phe Ile Arg Ile Asp Thr Ala Cys Val Cys Val Leu
            100                 105                 110

Ser Arg Lys Ala Val Arg Ala
            115                 120

<210> SEQ ID NO 4
<211> LENGTH: 120
<212> TYPE: PRT
<213> ORGANISM: Homo sapiens

<400> SEQUENCE: 4

Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Gly
            20                  25                  30

Gly Lys Glu Val Met Val Leu Gly Glu Val Asn Ile Asn Asn Ser Val
            35                  40                  45

Phe Lys Gln Tyr Phe Phe Glu Thr Lys Cys Arg Asp Pro Asn Pro Val
    50                  55                  60

Asp Ser Gly Cys Arg Gly Ile Asp Ser Lys His Trp Asn Ser Tyr Cys
65                  70                  75                  80

Thr Thr Thr His Thr Phe Val Lys Ala Leu Thr Met Asp Gly Lys Gln
            85                  90                  95

Ala Ala Trp Arg Phe Ile Arg Ile Asp Thr Ala Cys Val Cys Val Leu
            100                 105                 110

Ser Arg Lys Ala Val Arg Ala
            115                 120

<210> SEQ ID NO 5
<211> LENGTH: 120
<212> TYPE: PRT
<213> ORGANISM: Homo sapiens
```

<400> SEQUENCE: 5

Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Leu
            20                  25                  30

Gly Lys Glu Val Met Val Leu Gly Glu Val Asn Ile Asn Asn Ser Val
        35                  40                  45

Phe Lys Gln Tyr Phe Phe Glu Thr Lys Cys Arg Asp Pro Asn Pro Val
    50                  55                  60

Asp Ser Gly Cys Arg Gly Ile Asp Ser Lys His Trp Asn Ser Tyr Cys
65                  70                  75                  80

Thr Thr Thr His Thr Phe Val Lys Ala Leu Thr Met Asp Gly Lys Gln
                85                  90                  95

Ala Ala Trp Arg Phe Ile Arg Ile Asp Thr Ala Cys Val Cys Val Leu
            100                 105                 110

Ser Arg Lys Ala Val Arg Arg Ala
            115                 120

<210> SEQ ID NO 6
<211> LENGTH: 120
<212> TYPE: PRT
<213> ORGANISM: Homo sapiens

<400> SEQUENCE: 6

Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Tyr
            20                  25                  30

Gly Lys Glu Val Met Val Leu Gly Glu Val Asn Ile Asn Asn Ser Val
        35                  40                  45

Phe Lys Gln Tyr Phe Phe Glu Thr Lys Cys Arg Asp Pro Asn Pro Val
    50                  55                  60

Asp Ser Gly Cys Arg Gly Ile Asp Ser Lys His Trp Asn Ser Tyr Cys
65                  70                  75                  80

Thr Thr Thr His Thr Phe Val Lys Ala Leu Thr Met Asp Gly Lys Gln
                85                  90                  95

Ala Ala Trp Arg Phe Ile Arg Ile Asp Thr Ala Cys Val Cys Val Leu
            100                 105                 110

Ser Arg Lys Ala Val Arg Arg Ala
            115                 120

<210> SEQ ID NO 7
<211> LENGTH: 120
<212> TYPE: PRT
<213> ORGANISM: Homo sapiens

<400> SEQUENCE: 7

Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Lys
            20                  25                  30

Gly Lys Glu Val Met Val Leu Gly Glu Val Asn Ile Asn Asn Ser Val
        35                  40                  45

Phe Lys Gln Tyr Phe Phe Glu Thr Lys Cys Leu Asp Pro Asn Pro Val
    50                  55                  60

```
Asp Ser Gly Cys Arg Gly Ile Asp Ser Lys His Trp Asn Ser Tyr Cys
 65                  70                  75                  80

Thr Thr Thr His Thr Phe Val Lys Ala Leu Thr Met Asp Gly Lys Gln
                 85                  90                  95

Ala Ala Trp Arg Phe Ile Arg Ile Asp Thr Ala Cys Val Cys Val Leu
             100                 105                 110

Ser Arg Lys Ala Val Arg Arg Ala
         115                 120

<210> SEQ ID NO 8
<211> LENGTH: 120
<212> TYPE: PRT
<213> ORGANISM: Homo sapiens

<400> SEQUENCE: 8

Ser Ser Ser His Pro Ile Phe His Arg Gly Glu Phe Ser Val Cys Asp
  1               5                  10                  15

Ser Val Ser Val Trp Val Gly Asp Lys Thr Thr Ala Thr Asp Ile Lys
             20                  25                  30

Gly Lys Glu Val Met Val Leu Gly Glu Val Asn Ile Asn Asn Ser Val
         35                  40                  45

Phe Lys Gln Tyr Phe Phe Glu Thr Lys Cys Ala Asp Pro Asn Pro Val
     50                  55                  60

Asp Ser Gly Cys Arg Gly Ile Asp Ser Lys His Trp Asn Ser Tyr Cys
 65                  70                  75                  80

Thr Thr Thr His Thr Phe Val Lys Ala Leu Thr Met Asp Gly Lys Gln
                 85                  90                  95

Ala Ala Trp Arg Phe Ile Arg Ile Asp Thr Ala Cys Val Cys Val Leu
             100                 105                 110

Ser Arg Lys Ala Val Arg Arg Ala
         115                 120

<210> SEQ ID NO 9
<211> LENGTH: 120
<212> TYPE: PRT
<213> ORGANISM: Homo sapiens

<400> SEQUENCE: 9

Ser Ser Ser His Pro Ile Phe His Arg Gly Glu Phe Ser Val Cys Asp
  1               5                  10                  15

Ser Val Ser Val Trp Val Gly Asp Lys Thr Thr Ala Thr Asp Ile Lys
             20                  25                  30

Gly Lys Glu Val Met Val Leu Gly Glu Val Asn Ile Asn Asn Ser Val
         35                  40                  45

Phe Lys Gln Tyr Phe Phe Glu Thr Lys Cys Arg Asp Pro Asn Pro Val
     50                  55                  60

Ala Ser Gly Cys Arg Gly Ile Asp Ser Lys His Trp Asn Ser Tyr Cys
 65                  70                  75                  80

Thr Thr Thr His Thr Phe Val Lys Ala Leu Thr Met Asp Gly Lys Gln
                 85                  90                  95

Ala Ala Trp Arg Phe Ile Arg Ile Asp Thr Ala Cys Val Cys Val Leu
             100                 105                 110

Ser Arg Lys Ala Val Arg Arg Ala
         115                 120

<210> SEQ ID NO 10
<211> LENGTH: 120
```

```
<212> TYPE: PRT
<213> ORGANISM: Homo sapiens

<400> SEQUENCE: 10

Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Lys
            20                  25                  30

Gly Lys Glu Val Met Val Leu Gly Glu Val Asn Ile Asn Asn Ser Val
        35                  40                  45

Phe Lys Gln Tyr Phe Phe Glu Thr Lys Cys Arg Asp Pro Asn Pro Val
    50                  55                  60

Gly Ser Gly Cys Arg Gly Ile Asp Ser Lys His Trp Asn Ser Tyr Cys
65                  70                  75                  80

Thr Thr Thr His Thr Phe Val Lys Ala Leu Thr Met Asp Gly Lys Gln
                85                  90                  95

Ala Ala Trp Arg Phe Ile Arg Ile Asp Thr Ala Cys Val Cys Val Leu
            100                 105                 110

Ser Arg Lys Ala Val Arg Arg Ala
        115                 120

<210> SEQ ID NO 11
<211> LENGTH: 120
<212> TYPE: PRT
<213> ORGANISM: Homo sapiens

<400> SEQUENCE: 11

Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Lys
            20                  25                  30

Gly Lys Glu Val Met Val Leu Gly Glu Val Asn Ile Asn Asn Ser Val
        35                  40                  45

Phe Lys Gln Tyr Phe Phe Glu Thr Lys Cys Arg Asp Pro Asn Pro Val
    50                  55                  60

Asp Ser Gly Cys Arg Gly Ile Asp Ser Leu His Trp Asn Ser Tyr Cys
65                  70                  75                  80

Thr Thr Thr His Thr Phe Val Lys Ala Leu Thr Met Asp Gly Lys Gln
                85                  90                  95

Ala Ala Trp Arg Phe Ile Arg Ile Asp Thr Ala Cys Val Cys Val Leu
            100                 105                 110

Ser Arg Lys Ala Val Arg Arg Ala
        115                 120

<210> SEQ ID NO 12
<211> LENGTH: 120
<212> TYPE: PRT
<213> ORGANISM: Homo sapiens

<400> SEQUENCE: 12

Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Lys
            20                  25                  30

Gly Lys Glu Val Met Val Leu Gly Glu Val Asn Ile Asn Asn Ser Val
        35                  40                  45

Phe Lys Gln Tyr Phe Phe Glu Thr Lys Cys Arg Asp Pro Asn Pro Val
```

```
                    50                  55                  60
Asp Ser Gly Cys Arg Gly Ile Asp Ser Lys His Trp Asn Ser Tyr Cys
 65                  70                  75                  80

Thr Thr Thr His Thr Phe Val Phe Ala Leu Thr Met Asp Gly Lys Gln
                 85                  90                  95

Ala Ala Trp Arg Phe Ile Arg Ile Asp Thr Ala Cys Val Cys Val Leu
            100                 105                 110

Ser Arg Lys Ala Val Arg Arg Ala
            115                 120
```

<210> SEQ ID NO 13
<211> LENGTH: 120
<212> TYPE: PRT
<213> ORGANISM: Homo sapiens

<400> SEQUENCE: 13

```
Ser Ser Ser His Pro Ile Phe His Arg Gly Glu Phe Ser Val Cys Asp
 1               5                  10                  15

Ser Val Ser Val Trp Val Gly Asp Lys Thr Thr Ala Thr Asp Ile Lys
                 20                  25                  30

Gly Lys Glu Val Met Val Leu Gly Glu Val Asn Ile Asn Asn Ser Val
             35                  40                  45

Phe Lys Gln Tyr Phe Phe Glu Thr Lys Cys Arg Asp Pro Asn Pro Val
         50                  55                  60

Asp Ser Gly Cys Arg Gly Ile Asp Ser Lys His Trp Asn Ser Tyr Cys
 65                  70                  75                  80

Thr Thr Thr His Thr Phe Val Leu Ala Leu Thr Met Asp Gly Lys Gln
                 85                  90                  95

Ala Ala Trp Arg Phe Ile Arg Ile Asp Thr Ala Cys Val Cys Val Leu
            100                 105                 110

Ser Arg Lys Ala Val Arg Arg Ala
            115                 120
```

<210> SEQ ID NO 14
<211> LENGTH: 120
<212> TYPE: PRT
<213> ORGANISM: Homo sapiens

<400> SEQUENCE: 14

```
Ser Ser Ser His Pro Ile Phe His Arg Gly Glu Phe Ser Val Cys Asp
 1               5                  10                  15

Ser Val Ser Val Trp Val Gly Asp Lys Thr Thr Ala Thr Asp Ile Lys
                 20                  25                  30

Gly Lys Glu Val Met Val Leu Gly Glu Val Asn Ile Asn Asn Ser Val
             35                  40                  45

Phe Lys Gln Tyr Phe Phe Glu Thr Lys Cys Arg Asp Pro Asn Pro Val
         50                  55                  60

Asp Ser Gly Cys Arg Gly Ile Asp Ser Lys His Trp Asn Ser Tyr Cys
 65                  70                  75                  80

Thr Thr Thr His Thr Phe Val Glu Ala Leu Thr Met Asp Gly Lys Gln
                 85                  90                  95

Ala Ala Trp Arg Phe Ile Arg Ile Asp Thr Ala Cys Val Cys Val Leu
            100                 105                 110

Ser Arg Lys Ala Val Arg Arg Ala
            115                 120
```

<210> SEQ ID NO 15
<211> LENGTH: 120
<212> TYPE: PRT
<213> ORGANISM: Homo sapiens

<400> SEQUENCE: 15

Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Lys
            20                  25                  30

Gly Lys Glu Val Met Val Leu Gly Glu Val Asn Ile Asn Asn Ser Val
        35                  40                  45

Phe Lys Gln Tyr Phe Phe Glu Thr Lys Cys Arg Asp Pro Asn Pro Val
    50                  55                  60

Asp Ser Gly Cys Arg Gly Ile Asp Ser Lys His Trp Asn Ser Tyr Cys
65                  70                  75                  80

Thr Thr Thr His Thr Phe Val Gly Ala Leu Thr Met Asp Gly Lys Gln
                85                  90                  95

Ala Ala Trp Arg Phe Ile Arg Ile Asp Thr Ala Cys Val Cys Val Leu
            100                 105                 110

Ser Arg Lys Ala Val Arg Arg Ala
        115                 120

<210> SEQ ID NO 16
<211> LENGTH: 120
<212> TYPE: PRT
<213> ORGANISM: Homo sapiens

<400> SEQUENCE: 16

Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Lys
            20                  25                  30

Gly Lys Glu Val Met Val Leu Gly Glu Val Asn Ile Asn Asn Ser Val
        35                  40                  45

Phe Lys Gln Tyr Phe Phe Glu Thr Lys Cys Arg Asp Pro Asn Pro Val
    50                  55                  60

Asp Ser Gly Cys Arg Gly Ile Asp Ser Lys His Trp Asn Ser Tyr Cys
65                  70                  75                  80

Thr Thr Thr His Thr Phe Val Lys Ala Leu Thr Met Asp Gly Lys Glu
                85                  90                  95

Ala Ala Trp Arg Phe Ile Arg Ile Asp Thr Ala Cys Val Cys Val Leu
            100                 105                 110

Ser Arg Lys Ala Val Arg Arg Ala
        115                 120

<210> SEQ ID NO 17
<211> LENGTH: 120
<212> TYPE: PRT
<213> ORGANISM: Homo sapiens

<400> SEQUENCE: 17

Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Lys
            20                  25                  30

Gly Lys Glu Val Met Val Leu Gly Glu Val Asn Ile Asn Asn Ser Val
        35                  40                  45

Phe Lys Gln Tyr Phe Phe Glu Thr Lys Cys Arg Asp Pro Asn Pro Val
    50                  55                  60

Asp Ser Gly Cys Arg Gly Ile Asp Ser Lys His Trp Asn Ser Tyr Cys
65                  70                  75                  80

Thr Thr Thr His Thr Phe Val Lys Ala Leu Thr Met Asp Gly Lys Gln
                85                  90                  95

Ala Ala Trp Arg Phe Ile Arg Ile Asp Thr Ala Cys Val Cys Val Leu
            100                 105                 110

Ser Val Lys Ala Val Arg Arg Ala
            115                 120

<210> SEQ ID NO 18
<211> LENGTH: 120
<212> TYPE: PRT
<213> ORGANISM: Homo sapiens

<400> SEQUENCE: 18

Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Lys
            20                  25                  30

Gly Lys Glu Val Met Val Leu Gly Glu Val Asn Ile Asn Asn Ser Val
        35                  40                  45

Phe Lys Gln Tyr Phe Phe Glu Thr Lys Cys Arg Asp Pro Asn Pro Val
    50                  55                  60

Asp Ser Gly Cys Arg Gly Ile Asp Ser Lys His Trp Asn Ser Tyr Cys
65                  70                  75                  80

Thr Thr Thr His Thr Phe Val Lys Ala Leu Thr Met Asp Gly Lys Gln
                85                  90                  95

Ala Ala Trp Arg Phe Ile Arg Ile Asp Thr Ala Cys Val Cys Val Leu
            100                 105                 110

Ser Phe Lys Ala Val Arg Arg Ala
            115                 120

<210> SEQ ID NO 19
<211> LENGTH: 120
<212> TYPE: PRT
<213> ORGANISM: Homo sapiens

<400> SEQUENCE: 19

Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Lys
            20                  25                  30

Gly Lys Glu Val Met Val Leu Gly Glu Val Asn Ile Asn Asn Ser Val
        35                  40                  45

Phe Lys Gln Tyr Phe Phe Glu Thr Lys Cys Arg Asp Pro Asn Pro Val
    50                  55                  60

Asp Ser Gly Cys Arg Gly Ile Asp Ser Lys His Trp Asn Ser Tyr Cys
65                  70                  75                  80

Thr Thr Thr His Thr Phe Val Lys Ala Leu Thr Met Asp Gly Lys Gln
                85                  90                  95

Ala Ala Trp Arg Phe Ile Arg Ile Asp Thr Ala Cys Val Cys Val Leu
            100                 105                 110

Ser Gly Lys Ala Val Arg Arg Ala
            115                 120

<210> SEQ ID NO 20
<211> LENGTH: 120
<212> TYPE: PRT
<213> ORGANISM: Homo sapiens

<400> SEQUENCE: 20

Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Lys
            20                  25                  30

Gly Lys Glu Val Met Val Leu Gly Glu Val Asn Ile Asn Asn Ser Val
        35                  40                  45

Phe Lys Gln Tyr Phe Phe Glu Thr Lys Cys Arg Asp Pro Asn Pro Val
    50                  55                  60

Asp Ser Gly Cys Arg Gly Ile Asp Ser Lys His Trp Asn Ser Tyr Cys
65                  70                  75                  80

Thr Thr Thr His Thr Phe Val Lys Ala Leu Thr Met Asp Gly Lys Gln
                85                  90                  95

Ala Ala Trp Arg Phe Ile Arg Ile Asp Thr Ala Cys Val Cys Val Leu
            100                 105                 110

Ser Leu Lys Ala Val Arg Arg Ala
        115                 120

<210> SEQ ID NO 21
<211> LENGTH: 120
<212> TYPE: PRT
<213> ORGANISM: Homo sapiens

<400> SEQUENCE: 21

Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Lys
            20                  25                  30

Gly Lys Glu Val Met Val Leu Gly Glu Val Asn Ile Asn Asn Ser Val
        35                  40                  45

Phe Lys Gln Tyr Phe Phe Glu Thr Lys Cys Arg Asp Pro Asn Pro Val
    50                  55                  60

Asp Ser Gly Cys Arg Gly Ile Asp Ser Lys His Trp Asn Ser Tyr Cys
65                  70                  75                  80

Thr Thr Thr His Thr Phe Val Lys Ala Leu Thr Met Asp Gly Lys Gln
                85                  90                  95

Ala Ala Trp Arg Ala Ile Arg Ile Asp Thr Ala Cys Val Cys Val Leu
            100                 105                 110

Ser Arg Lys Ala Val Arg Arg Ala
        115                 120

<210> SEQ ID NO 22
<211> LENGTH: 726
<212> TYPE: DNA
<213> ORGANISM: Homo sapiens

<400> SEQUENCE: 22
atgtccatgt tgttctacac tctgatcaca gcttttctga tcggcataca ggcggaacca      60
cactcagaga gcaatgtccc tgcaggacac accatccccc aagcccactg gactaaactt     120
cagcattccc ttgacactgc ccttcgcaga gcccgcagcg ccccggcagc ggcgatagct     180

| | |
|---|---|
| gcacgcgtgg cggggcagac ccgcaacatt actgtggacc ccaggctgtt taaaaagcgg | 240 |
| cgactccgtt caccccgtgt gctgtttagc acccagcctc cccgtgaagc tgcagacact | 300 |
| caggatctgg acttcgaggt cggtggtgct gccccttca acaggactca caggagcaag | 360 |
| cggtcatcat cccatcccat cttccacagg ggcgaagagt cggtgtgtga cagtgtcagc | 420 |
| gtgtgggttg gggataagac caccgccaca gacatcaagg gcaaggaggt gatggtgttg | 480 |
| ggagaggtga acattaacaa cagtgtattc aaacagtact tttttgagac caagtgccgg | 540 |
| gacccaaatc ccgttgacag cgggtgccgg ggcattgact caaagcactg gaactcatat | 600 |
| tgtaccacga ctcacacctt tgtcaaggcg ctgaccatgg atggcaagca ggctgcctgg | 660 |
| cggtttatcc ggatagatac ggcctgtgtg tgtgtgctca gcaggaaggc tgtgagaaga | 720 |
| gcctga | 726 |

<210> SEQ ID NO 23
<211> LENGTH: 726
<212> TYPE: DNA
<213> ORGANISM: Homo sapiens

<400> SEQUENCE: 23

| | |
|---|---|
| atgtccatgt tgttctacac tctgatcaca gcttttctga tcggcataca ggcggaacca | 60 |
| cactcagaga gcaatgtccc tgcaggacac accatccccc aagcccactg gactaaactt | 120 |
| cagcattccc ttgacactgc ccttcgcaga gcccgcagcg ccccggcagc ggcgatagct | 180 |
| gcacgcgtgg cggggcagac ccgcaacatt actgtggacc ccaggctgtt taaaaagcgg | 240 |
| cgactccgtt caccccgtgt gctgtttagc acccagcctc cccgtgaagc tgcagacact | 300 |
| caggatctgg acttcgaggt cggtggtgct gccccttca acaggactca caggagcaag | 360 |
| cggtcatcat cccatcccat cttccacagg ggcgaattct cggtgtgtga cagtgtcagc | 420 |
| gtgtgggttg gggataagac caccgccaca gacatcgggg gcaaggaggt gatggtgttg | 480 |
| ggagaggtga acattaacaa cagtgtattc aaacagtact tttttgagac caagtgccgg | 540 |
| gacccaaatc ccgttgacag cgggtgccgg ggcattgact caaagcactg gaactcatat | 600 |
| tgtaccacga ctcacacctt tgtcaaggcg ctgaccatgg atggcaagca ggctgcctgg | 660 |
| cggtttatcc ggatagatac ggcctgtgtg tgtgtgctca gcaggaaggc tgtgagaaga | 720 |
| gcctga | 726 |

<210> SEQ ID NO 24
<211> LENGTH: 726
<212> TYPE: DNA
<213> ORGANISM: Homo sapiens

<400> SEQUENCE: 24

| | |
|---|---|
| atgtccatgt tgttctacac tctgatcaca gcttttctga tcggcataca ggcggaacca | 60 |
| cactcagaga gcaatgtccc tgcaggacac accatccccc aagcccactg gactaaactt | 120 |
| cagcattccc ttgacactgc ccttcgcaga gcccgcagcg ccccggcagc ggcgatagct | 180 |
| gcacgcgtgg cggggcagac ccgcaacatt actgtggacc ccaggctgtt taaaaagcgg | 240 |
| cgactccgtt caccccgtgt gctgtttagc acccagcctc cccgtgaagc tgcagacact | 300 |
| caggatctgg acttcgaggt cggtggtgct gccccttca acaggactca caggagcaag | 360 |
| cggtcatcat cccatcccat cttccacagg ggcgaattct cggtgtgtga cagtgtcagc | 420 |
| gtgtgggttg gggataagac caccgccaca gacatcctgg gcaaggaggt gatggtgttg | 480 |
| ggagaggtga acattaacaa cagtgtattc aaacagtact tttttgagac caagtgccgg | 540 |

| | |
|---|---|
| gacccaaatc ccgttgacag cgggtgccgg ggcattgact caaagcactg gaactcatat | 600 |
| tgtaccacga ctcacacctt tgtcaaggcg ctgaccatgg atggcaagca ggctgcctgg | 660 |
| cggtttatcc ggatagatac ggcctgtgtg tgtgtgctca gcaggaaggc tgtgagaaga | 720 |
| gcctga | 726 |

<210> SEQ ID NO 25
<211> LENGTH: 726
<212> TYPE: DNA
<213> ORGANISM: Homo sapiens

<400> SEQUENCE: 25

| | |
|---|---|
| atgtccatgt tgttctacac tctgatcaca gcttttctga tcggcataca ggcggaacca | 60 |
| cactcagaga gcaatgtccc tgcaggacac accatccccc aagcccactg gactaaactt | 120 |
| cagcattccc ttgacactgc ccttcgcaga gcccgcagcg ccccggcagc ggcgatagct | 180 |
| gcacgcgtgg cggggcagac ccgcaacatt actgtggacc ccaggctgtt taaaaagcgg | 240 |
| cgactccgtt caccccgtgt gctgtttagc acccagcctc cccgtgaagc tgcagacact | 300 |
| caggatctgg acttcgaggt cggtggtgct gccccttca acaggactca caggagcaag | 360 |
| cggtcatcat cccatcccat cttccacagg ggcgaattct cggtgtgtga cagtgtcagc | 420 |
| gtgtgggttg gggataagac caccgccaca gacatctacg caaggaggt gatggtgttg | 480 |
| ggagaggtga acattaacaa cagtgtattc aaacagtact tttttgagac caagtgccgg | 540 |
| gacccaaatc ccgttgacag cgggtgccgg ggcattgact caaagcactg gaactcatat | 600 |
| tgtaccacga ctcacacctt tgtcaaggcg ctgaccatgg atggcaagca ggctgcctgg | 660 |
| cggtttatcc ggatagatac ggcctgtgtg tgtgtgctca gcaggaaggc tgtgagaaga | 720 |
| gcctga | 726 |

<210> SEQ ID NO 26
<211> LENGTH: 726
<212> TYPE: DNA
<213> ORGANISM: Homo sapiens

<400> SEQUENCE: 26

| | |
|---|---|
| atgtccatgt tgttctacac tctgatcaca gcttttctga tcggcataca ggcggaacca | 60 |
| cactcagaga gcaatgtccc tgcaggacac accatccccc aagcccactg gactaaactt | 120 |
| cagcattccc ttgacactgc ccttcgcaga gcccgcagcg ccccggcagc ggcgatagct | 180 |
| gcacgcgtgg cggggcagac ccgcaacatt actgtggacc ccaggctgtt taaaaagcgg | 240 |
| cgactccgtt caccccgtgt gctgtttagc acccagcctc cccgtgaagc tgcagacact | 300 |
| caggatctgg acttcgaggt cggtggtgct gccccttca acaggactca caggagcaag | 360 |
| cggtcatcat cccatcccat cttccacagg ggcgaattct cggtgtgtga cagtgtcagc | 420 |
| gtgtgggttg gggataagac caccgccaca gacatcaagg caaggaggt gatggtgttg | 480 |
| ggagaggtga acattaacaa cagtgtattc aaacagtact tttttgagac caagtgcctg | 540 |
| gacccaaatc ccgttgacag cgggtgccgg ggcattgact caaagcactg gaactcatat | 600 |
| tgtaccacga ctcacacctt tgtcaaggcg ctgaccatgg atggcaagca ggctgcctgg | 660 |
| cggtttatcc ggatagatac ggcctgtgtg tgtgtgctca gcaggaaggc tgtgagaaga | 720 |
| gcctga | 726 |

<210> SEQ ID NO 27

```
<211> LENGTH: 726
<212> TYPE: DNA
<213> ORGANISM: Homo sapiens

<400> SEQUENCE: 27
atgtccatgt tgttctacac tctgatcaca gcttttctga tcggcataca ggcggaacca      60
cactcagaga gcaatgtccc tgcaggacac accatccccc aagcccactg gactaaactt     120
cagcattccc ttgacactgc ccttcgcaga gcccgcagcg ccccggcagc ggcgatagct     180
gcacgcgtgg cggggcagac ccgcaacatt actgtggacc ccaggctgtt taaaaagcgg     240
cgactccgtt caccccgtgt gctgtttagc acccagcctc cccgtgaagc tgcagacact     300
caggatctgg acttcgaggt cggtggtgct gccccttca acaggactca caggagcaag     360
cggtcatcat cccatcccat cttccacagg ggcgaattct cggtgtgtga cagtgtcagc     420
gtgtgggttg gggataagac caccgccaca gacatcaagg gcaaggaggt gatggtgttg     480
ggagaggtga acattaacaa cagtgtattc aaacagtact tttttgagac caagtgcgcg     540
gacccaaatc ccgttgacag cgggtgccgg ggcattgact caaagcactg gaactcatat     600
tgtaccacga ctcacacctt tgtcaaggcg ctgaccatgg atggcaagca ggctgcctgg     660
cggtttatcc ggatagatac ggcctgtgtg tgtgtgctca gcaggaaggc tgtgagaaga     720
gcctga                                                                726

<210> SEQ ID NO 28
<211> LENGTH: 726
<212> TYPE: DNA
<213> ORGANISM: Homo sapiens

<400> SEQUENCE: 28
atgtccatgt tgttctacac tctgatcaca gcttttctga tcggcataca ggcggaacca      60
cactcagaga gcaatgtccc tgcaggacac accatccccc aagcccactg gactaaactt     120
cagcattccc ttgacactgc ccttcgcaga gcccgcagcg ccccggcagc ggcgatagct     180
gcacgcgtgg cggggcagac ccgcaacatt actgtggacc ccaggctgtt taaaaagcgg     240
cgactccgtt caccccgtgt gctgtttagc acccagcctc cccgtgaagc tgcagacact     300
caggatctgg acttcgaggt cggtggtgct gccccttca acaggactca caggagcaag     360
cggtcatcat cccatcccat cttccacagg ggcgaattct cggtgtgtga cagtgtcagc     420
gtgtgggttg gggataagac caccgccaca gacatcaagg gcaaggaggt gatggtgttg     480
ggagaggtga acattaacaa cagtgtattc aaacagtact tttttgagac caagtgccgg     540
gacccaaatc ccgttgccag cgggtgccgg ggcattgact caaagcactg gaactcatat     600
tgtaccacga ctcacacctt tgtcaaggcg ctgaccatgg atggcaagca ggctgcctgg     660
cggtttatcc ggatagatac ggcctgtgtg tgtgtgctca gcaggaaggc tgtgagaaga     720
gcctga                                                                726

<210> SEQ ID NO 29
<211> LENGTH: 726
<212> TYPE: DNA
<213> ORGANISM: Homo sapiens

<400> SEQUENCE: 29
atgtccatgt tgttctacac tctgatcaca gcttttctga tcggcataca ggcggaacca      60
cactcagaga gcaatgtccc tgcaggacac accatccccc aagcccactg gactaaactt     120
cagcattccc ttgacactgc ccttcgcaga gcccgcagcg ccccggcagc ggcgatagct     180
```

```
gcacgcgtgg cggggcagac ccgcaacatt actgtggacc ccaggctgtt taaaaagcgg      240
cgactccgtt caccccgtgt gctgtttagc acccagcctc cccgtgaagc tgcagacact      300
caggatctgg acttcgaggt cggtggtgct gccccttca acaggactca caggagcaag       360
cggtcatcat cccatcccat cttccacagg ggcgaattct cggtgtgtga cagtgtcagc      420
gtgtgggttg gggataagac caccgccaca gacatcaagg gcaaggaggt gatggtgttg      480
ggagaggtga acattaacaa cagtgtattc aaacagtact tttttgagac caagtgccgg     540
gacccaaatc ccgttggcag cgggtgccgg ggcattgact caaagcactg gaactcatat      600
tgtaccacga ctcacacctt tgtcaaggcg ctgaccatgg atggcaagca ggctgcctgg      660
cggtttatcc ggatagatac ggcctgtgtg tgtgtgctca gcaggaaggc tgtgagaaga      720
gcctga                                                                 726

<210> SEQ ID NO 30
<211> LENGTH: 726
<212> TYPE: DNA
<213> ORGANISM: Homo sapiens

<400> SEQUENCE: 30
atgtccatgt tgttctacac tctgatcaca gcttttctga tcggcataca ggcggaacca      60
cactcagaga gcaatgtccc tgcaggacac accatccccc aagcccactg gactaaactt      120
cagcattccc ttgacactgc ccttcgcaga gcccgcagcg ccccggcagc ggcgatagct      180
gcacgcgtgg cggggcagac ccgcaacatt actgtggacc ccaggctgtt taaaaagcgg      240
cgactccgtt caccccgtgt gctgtttagc acccagcctc cccgtgaagc tgcagacact      300
caggatctgg acttcgaggt cggtggtgct gccccttca acaggactca caggagcaag       360
cggtcatcat cccatcccat cttccacagg ggcgaattct cggtgtgtga cagtgtcagc      420
gtgtgggttg gggataagac caccgccaca gacatcaagg gcaaggaggt gatggtgttg      480
ggagaggtga acattaacaa cagtgtattc aaacagtact tttttgagac caagtgccgg     540
gacccaaatc ccgttgacag cgggtgccgg ggcattgact cattgcactg gaactcatat      600
tgtaccacga ctcacacctt tgtcaaggcg ctgaccatgg atggcaagca ggctgcctgg      660
cggtttatcc ggatagatac ggcctgtgtg tgtgtgctca gcaggaaggc tgtgagaaga      720
gcctga                                                                 726

<210> SEQ ID NO 31
<211> LENGTH: 726
<212> TYPE: DNA
<213> ORGANISM: Homo sapiens

<400> SEQUENCE: 31
atgtccatgt tgttctacac tctgatcaca gcttttctga tcggcataca ggcggaacca      60
cactcagaga gcaatgtccc tgcaggacac accatccccc aagcccactg gactaaactt      120
cagcattccc ttgacactgc ccttcgcaga gcccgcagcg ccccggcagc ggcgatagct      180
gcacgcgtgg cggggcagac ccgcaacatt actgtggacc ccaggctgtt taaaaagcgg      240
cgactccgtt caccccgtgt gctgtttagc acccagcctc cccgtgaagc tgcagacact      300
caggatctgg acttcgaggt cggtggtgct gccccttca acaggactca caggagcaag       360
cggtcatcat cccatcccat cttccacagg ggcgaattct cggtgtgtga cagtgtcagc      420
gtgtgggttg gggataagac caccgccaca gacatcaagg gcaaggaggt gatggtgttg      480
```

```
ggagaggtga acattaacaa cagtgtattc aaacagtact tttttgagac caagtgccgg    540
gacccaaatc ccgttgacag cgggtgccgg ggcattgact caaagcactg gaactcatat    600
tgtaccacga ctcacacctt tgtctttgcg ctgaccatgg atggcaagca ggctgcctgg    660
cggtttatcc ggatagatac ggcctgtgtg tgtgtgctca gcaggaaggc tgtgagaaga    720
gcctga                                                               726
```

<210> SEQ ID NO 32
<211> LENGTH: 726
<212> TYPE: DNA
<213> ORGANISM: Homo sapiens

<400> SEQUENCE: 32

```
atgtccatgt tgttctacac tctgatcaca gctttctga tcggcataca ggcggaacca     60
cactcagaga gcaatgtccc tgcaggacac accatccccc aagcccactg gactaaactt    120
cagcattccc ttgacactgc ccttcgcaga gcccgcagcg ccccggcagc ggcgatagct    180
gcacgcgtgg cggggcagac ccgcaacatt actgtggacc ccaggctgtt taaaaagcgg    240
cgactccgtt caccccgtgt gctgtttagc acccagcctc cccgtgaagc tgcagacact    300
caggatctgg acttcgaggt cggtggtgct gccccttca acaggactca caggagcaag    360
cggtcatcat cccatcccat cttccacagg ggcgaattct cggtgtgtga cagtgtcagc    420
gtgtgggttg gggataagac caccgccaca gacatcaagg gcaaggaggt gatggtgttg    480
ggagaggtga acattaacaa cagtgtattc aaacagtact tttttgagac caagtgccgg    540
gacccaaatc ccgttgacag cgggtgccgg ggcattgact caaagcactg gaactcatat    600
tgtaccacga ctcacacctt tgtcttggcg ctgaccatgg atggcaagca ggctgcctgg    660
cggtttatcc ggatagatac ggcctgtgtg tgtgtgctca gcaggaaggc tgtgagaaga    720
gcctga                                                               726
```

<210> SEQ ID NO 33
<211> LENGTH: 726
<212> TYPE: DNA
<213> ORGANISM: Homo sapiens

<400> SEQUENCE: 33

```
atgtccatgt tgttctacac tctgatcaca gctttctga tcggcataca ggcggaacca     60
cactcagaga gcaatgtccc tgcaggacac accatccccc aagcccactg gactaaactt    120
cagcattccc ttgacactgc ccttcgcaga gcccgcagcg ccccggcagc ggcgatagct    180
gcacgcgtgg cggggcagac ccgcaacatt actgtggacc ccaggctgtt taaaaagcgg    240
cgactccgtt caccccgtgt gctgtttagc acccagcctc cccgtgaagc tgcagacact    300
caggatctgg acttcgaggt cggtggtgct gccccttca acaggactca caggagcaag    360
cggtcatcat cccatcccat cttccacagg ggcgaattct cggtgtgtga cagtgtcagc    420
gtgtgggttg gggataagac caccgccaca gacatcaagg gcaaggaggt gatggtgttg    480
ggagaggtga acattaacaa cagtgtattc aaacagtact tttttgagac caagtgccgg    540
gacccaaatc ccgttgacag cgggtgccgg ggcattgact caaagcactg gaactcatat    600
tgtaccacga ctcacacctt tgtcgaggcg ctgaccatgg atggcaagca ggctgcctgg    660
cggtttatcc ggatagatac ggcctgtgtg tgtgtgctca gcaggaaggc tgtgagaaga    720
gcctga                                                               726
```

<210> SEQ ID NO 34
<211> LENGTH: 726
<212> TYPE: DNA
<213> ORGANISM: Homo sapiens

<400> SEQUENCE: 34

| | | | | | |
|---|---|---|---|---|---|
| atgtccatgt | tgttctacac | tctgatcaca | gcttttctga | tcggcataca | ggcggaacca | 60 |
| cactcagaga | gcaatgtccc | tgcaggacac | accatccccc | aagcccactg | gactaaactt | 120 |
| cagcattccc | ttgacactgc | ccttcgcaga | gcccgcagcg | ccccggcagc | ggcgatagct | 180 |
| gcacgcgtgg | cggggcagac | ccgcaacatt | actgtggacc | ccaggctgtt | taaaaagcgg | 240 |
| cgactccgtt | caccccgtgt | gctgtttagc | acccagcctc | cccgtgaagc | tgcagacact | 300 |
| caggatctgg | acttcgaggt | cggtggtgct | gccccttca | acaggactca | caggagcaag | 360 |
| cggtcatcat | cccatcccat | cttccacagg | ggcgaattct | cggtgtgtga | cagtgtcagc | 420 |
| gtgtgggttg | gggataagac | caccgccaca | gacatcaagg | gcaaggaggt | gatggtgttg | 480 |
| ggagaggtga | acattaacaa | cagtgtattc | aaacagtact | tttttgagac | caagtgccgg | 540 |
| gacccaaatc | ccgttgacag | cgggtgccgg | ggcattgact | caaagcactg | gaactcatat | 600 |
| tgtaccacga | ctcacacctt | tgtcggggcg | ctgaccatgg | atggcaagca | ggctgcctgg | 660 |
| cggtttatcc | ggatagatac | ggcctgtgtg | tgtgtgctca | gcaggaaggc | tgtgagaaga | 720 |
| gcctga | | | | | | 726 |

<210> SEQ ID NO 35
<211> LENGTH: 726
<212> TYPE: DNA
<213> ORGANISM: Homo sapiens

<400> SEQUENCE: 35

| | | | | | |
|---|---|---|---|---|---|
| atgtccatgt | tgttctacac | tctgatcaca | gcttttctga | tcggcataca | ggcggaacca | 60 |
| cactcagaga | gcaatgtccc | tgcaggacac | accatccccc | aagcccactg | gactaaactt | 120 |
| cagcattccc | ttgacactgc | ccttcgcaga | gcccgcagcg | ccccggcagc | ggcgatagct | 180 |
| gcacgcgtgg | cggggcagac | ccgcaacatt | actgtggacc | ccaggctgtt | taaaaagcgg | 240 |
| cgactccgtt | caccccgtgt | gctgtttagc | acccagcctc | cccgtgaagc | tgcagacact | 300 |
| caggatctgg | acttcgaggt | cggtggtgct | gccccttca | acaggactca | caggagcaag | 360 |
| cggtcatcat | cccatcccat | cttccacagg | ggcgaattct | cggtgtgtga | cagtgtcagc | 420 |
| gtgtgggttg | gggataagac | caccgccaca | gacatcaagg | gcaaggaggt | gatggtgttg | 480 |
| ggagaggtga | acattaacaa | cagtgtattc | aaacagtact | tttttgagac | caagtgccgg | 540 |
| gacccaaatc | ccgttgacag | cgggtgccgg | ggcattgact | caaagcactg | gaactcatat | 600 |
| tgtaccacga | ctcacacctt | tgtcaaggcg | ctgaccatgg | atggcaagga | ggctgcctgg | 660 |
| cggtttatcc | ggatagatac | ggcctgtgtg | tgtgtgctca | gcaggaaggc | tgtgagaaga | 720 |
| gcctga | | | | | | 726 |

<210> SEQ ID NO 36
<211> LENGTH: 726
<212> TYPE: DNA
<213> ORGANISM: Homo sapiens

<400> SEQUENCE: 36

| | | | | | |
|---|---|---|---|---|---|
| atgtccatgt | tgttctacac | tctgatcaca | gcttttctga | tcggcataca | ggcggaacca | 60 |
| cactcagaga | gcaatgtccc | tgcaggacac | accatccccc | aagcccactg | gactaaactt | 120 |

```
cagcattccc ttgacactgc ccttcgcaga gcccgcagcg ccccggcagc ggcgatagct      180
gcacgcgtgg cggggcagac ccgcaacatt actgtggacc ccaggctgtt taaaaagcgg      240
cgactccgtt caccccgtgt gctgtttagc acccagcctc cccgtgaagc tgcagacact      300
caggatctgg acttcgaggt cggtggtgct gccccccttca acaggactca caggagcaag      360
cggtcatcat cccatcccat cttccacagg ggcgaattct cggtgtgtga cagtgtcagc      420
gtgtgggttg gggataagac caccgccaca gacatcaagg gcaaggaggt gatggtgttg      480
ggagaggtga acattaacaa cagtgtattc aaacagtact ttttgagac caagtgccgg      540 gacccaaatc ccgttgacag cgggtgccgg ggcattgact caaagcactg gaactcatat      600
tgtaccacga ctcacacctt tgtcaaggcg ctgaccatgg atggcaagca ggctgcctgg      660
cggtttatcc ggatagatac ggcctgtgtg tgtgtgctca gcgtcaaggc tgtgagaaga      720
gcctga                                                                 726

<210> SEQ ID NO 37
<211> LENGTH: 726
<212> TYPE: DNA
<213> ORGANISM: Homo sapiens

<400> SEQUENCE: 37
atgtccatgt tgttctacac tctgatcaca gcttttctga tcggcataca ggcggaacca       60
cactcagaga gcaatgtccc tgcaggacac accatccccc aagcccactg gactaaactt      120
cagcattccc ttgacactgc ccttcgcaga gcccgcagcg ccccggcagc ggcgatagct      180
gcacgcgtgg cggggcagac ccgcaacatt actgtggacc ccaggctgtt taaaaagcgg      240
cgactccgtt caccccgtgt gctgtttagc acccagcctc cccgtgaagc tgcagacact      300
caggatctgg acttcgaggt cggtggtgct gccccccttca acaggactca caggagcaag      360
cggtcatcat cccatcccat cttccacagg ggcgaattct cggtgtgtga cagtgtcagc      420
gtgtgggttg gggataagac caccgccaca gacatcaagg gcaaggaggt gatggtgttg      480
ggagaggtga acattaacaa cagtgtattc aaacagtact ttttgagac caagtgccgg      540 gacccaaatc ccgttgacag cgggtgccgg ggcattgact caaagcactg gaactcatat      600
tgtaccacga ctcacacctt tgtcaaggcg ctgaccatgg atggcaagca ggctgcctgg      660
cggtttatcc ggatagatac ggcctgtgtg tgtgtgctca gcttcaaggc tgtgagaaga      720
gcctga                                                                 726

<210> SEQ ID NO 38
<211> LENGTH: 726
<212> TYPE: DNA
<213> ORGANISM: Homo sapiens

<400> SEQUENCE: 38
atgtccatgt tgttctacac tctgatcaca gcttttctga tcggcataca ggcggaacca       60
cactcagaga gcaatgtccc tgcaggacac accatccccc aagcccactg gactaaactt      120
cagcattccc ttgacactgc ccttcgcaga gcccgcagcg ccccggcagc ggcgatagct      180
gcacgcgtgg cggggcagac ccgcaacatt actgtggacc ccaggctgtt taaaaagcgg      240
cgactccgtt caccccgtgt gctgtttagc acccagcctc cccgtgaagc tgcagacact      300
caggatctgg acttcgaggt cggtggtgct gccccccttca acaggactca caggagcaag      360
cggtcatcat cccatcccat cttccacagg ggcgaattct cggtgtgtga cagtgtcagc      420
gtgtgggttg gggataagac caccgccaca gacatcaagg gcaaggaggt gatggtgttg      480
```

| | | |
|---|---|---|
| ggagaggtga acattaacaa cagtgtattc aaacagtact tttttgagac caagtgccgg | 540 | |
| gacccaaatc ccgttgacag cgggtgccgg ggcattgact caaagcactg gaactcatat | 600 | |
| tgtaccacga ctcacacctt tgtcaaggcg ctgaccatgg atggcaagca ggctgcctgg | 660 | |
| cggtttatcc ggatagatac ggcctgtgtg tgtgtgctca gcgggaaggc tgtgagaaga | 720 | |
| gcctga | 726 | |

<210> SEQ ID NO 39
<211> LENGTH: 726
<212> TYPE: DNA
<213> ORGANISM: Homo sapiens

<400> SEQUENCE: 39

| | | |
|---|---|---|
| atgtccatgt tgttctacac tctgatcaca gcttttctga tcggcataca ggcggaacca | 60 | |
| cactcagaga gcaatgtccc tgcaggacac accatccccc aagcccactg gactaaactt | 120 | |
| cagcattccc ttgacactgc ccttcgcaga gcccgcagcg ccccggcagc ggcgatagct | 180 | |
| gcacgcgtgg cggggcagac ccgcaacatt actgtggacc ccaggctgtt taaaaagcgg | 240 | |
| cgactccgtt caccccgtgt gctgtttagc acccagcctc cccgtgaagc tgcagacact | 300 | |
| caggatctgg acttcgaggt cggtggtgct gccccttca acaggactca caggagcaag | 360 | |
| cggtcatcat cccatcccat cttccacagg ggcgaattct cggtgtgtga cagtgtcagc | 420 | |
| gtgtgggttg gggataagac caccgccaca gacatcaagg gcaaggaggt gatggtgttg | 480 | |
| ggagaggtga acattaacaa cagtgtattc aaacagtact tttttgagac caagtgccgg | 540 | |
| gacccaaatc ccgttgacag cgggtgccgg ggcattgact caaagcactg gaactcatat | 600 | |
| tgtaccacga ctcacacctt tgtcaaggcg ctgaccatgg atggcaagca ggctgcctgg | 660 | |
| cggtttatcc ggatagatac ggcctgtgtg tgtgtgctca gcttgaaggc tgtgagaaga | 720 | |
| gcctga | 726 | |

<210> SEQ ID NO 40
<211> LENGTH: 726
<212> TYPE: DNA
<213> ORGANISM: Homo sapiens

<400> SEQUENCE: 40

| | | |
|---|---|---|
| atgtccatgt tgttctacac tctgatcaca gcttttctga tcggcataca ggcggaacca | 60 | |
| cactcagaga gcaatgtccc tgcaggacac accatccccc aagcccactg gactaaactt | 120 | |
| cagcattccc ttgacactgc ccttcgcaga gcccgcagcg ccccggcagc ggcgatagct | 180 | |
| gcacgcgtgg cggggcagac ccgcaacatt actgtggacc ccaggctgtt taaaaagcgg | 240 | |
| cgactccgtt caccccgtgt gctgtttagc acccagcctc cccgtgaagc tgcagacact | 300 | |
| caggatctgg acttcgaggt cggtggtgct gccccttca acaggactca caggagcaag | 360 | |
| cggtcatcat cccatcccat cttccacagg ggcgaattct cggtgtgtga cagtgtcagc | 420 | |
| gtgtgggttg gggataagac caccgccaca gacatcaagg gcaaggaggt gatggtgttg | 480 | |
| ggagaggtga acattaacaa cagtgtattc aaacagtact tttttgagac caagtgccgg | 540 | |
| gacccaaatc ccgttgacag cgggtgccgg ggcattgact caaagcactg gaactcatat | 600 | |
| tgtaccacga ctcacacctt tgtcaaggcg ctgaccatgg atggcaagca ggctgcctgg | 660 | |
| cgggcgatcc ggatagatac ggcctgtgtg tgtgtgctca gcaggaaggc tgtgagaaga | 720 | |
| gcctga | 726 | |

```
<210> SEQ ID NO 41
<211> LENGTH: 19
<212> TYPE: DNA
<213> ORGANISM: Artificial sequence
<220> FEATURE:
<223> OTHER INFORMATION: primer F

<400> SEQUENCE: 41
ggaattcatg tccatgttg                                              19

<210> SEQ ID NO 42
<211> LENGTH: 19
<212> TYPE: DNA
<213> ORGANISM: Artificial sequence
<220> FEATURE:
<223> OTHER INFORMATION: primer R

<400> SEQUENCE: 42
caagctttca ggctcttct                                              19
```

NERVE GROWTH FACTOR MUTANT

CROSS REFERENCE TO RELATED APPLICATIONS

This application is a U.S. National Phase Application of PCT International Application Number PCT/CN2017/077038, filed on Mar. 17, 2017, designating the United States of America and published in the Chinese language, which is an International Application of and claims the benefit of priority to Chinese Patent Application No. 201610159303.7, filed on Mar. 18, 2016. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is SeqList-DRGN005-002APC.txt, the date of creation of the ASCII text file is Aug. 27, 2018, and the size of the ASCII text file is 43 KB.

TECHNICAL FIELD

The present disclosure relates to a nerve growth factor mutant, and belongs to the field of biopharmaceuticals.

BACKGROUND

Pain may be divided into two types: sensory pain and neuropathic pain according to its neurophysiological mechanism. The former is directly caused by noxious stimulation, relates to tissue damage or inflammatory reaction, and is also known as inflammatory pain. The latter is a chronic pain directly caused by the damage or disease of somatosensory nervous system.

Nerve Growth Factor (NGF) is the first neurotrophic factor discovered in mouse sarcoma cells by Italian scientist Levi-Monticini in 1953. NGF is a neuronal growth regulator having a dual biological function of neuron nutrition and promoting neurite growth, which plays an important regulatory role in the development, differentiation, growth, regeneration, and expression of functional properties of central and peripheral neurons. NGF includes three subunits of α, β, and γ. The β subunit is an active region, which is formed by combining two single chains through a non-covalent bond. Levi-Montalcini won the Nobel Prize for discovering NGF. At present, a number of NGF products have been marketed at home and abroad, and are mainly used for the treatment of nervous system dysplasia, including amblyopia, neuroma, various nerve injuries and nervous system diseases.

NGF is present in a variety of species and is abundant in male mouse submandibular gland, bovine seminal plasma, snake venom, guinea pig prostate, and human placental tissue. The amino acid sequence homology between mouse NGF and human NGF is up to 90%. In consideration of the species diversity of mouse NGF applied to human body, the risk of the potential pathogenic factor of a mouse as a raw material and the limitation of human placenta tissue raw material, there is a very good application prospect for the development of the genetic engineering technology for preparing recombinant human NGF (rhNGF) to replace the extracted mouse NGF and human NGF.

Mature NGF in vivo exists as a homodimer, in which each peptide chain includes 120 amino acids. The human NGF gene is located on a short arm of chromosome 1, and the complete NGF exon consists of 241 amino acids, commonly referred to as a prepro NGF precursor. The signal peptide of the prepro NGF precursor in the endoplasmic reticulum is cleaved to form a pro NGF precursor (223 amino acids). The pro NGF precursor exists in a form of a homodimer in the endoplasmic reticulum, and then transferred to a golgi apparatus, in which the precursor undergoes digestion with Furin to form a mature NGF dimer (the monomer contains 120 amino acids) which is then transported outside the cell. Meanwhile, some uncleaved pro NGF precursors are secreted outside the cell.

Recombinant human NGF avoids some potential pathogenic risks, but there are still major problems in actual application: 1) as for maintaining the biological activity of NGF, like other proteins, the biological activity of NGF depends on the secondary and tertiary structures thereof, and thus it is particularly important to maintain its biological activity during preparation, purification, storage and administration; and 2) NGF may cause serious pain, which cannot be tolerated by some patients, during application, thereby partially limiting its use. NGF is involved in the pathophysiological process of pain through affecting the release of inflammatory mediators, the opening of ion channels, and promoting the growth of nerve fibers to cause pain; and involved in the development of pain through regulating ion channels and molecular signals. Some scholars speculate that NGF may also cause pain through promoting the expression of pain-inducing substances, and may change the budding and regeneration of neurons after injury of organism. Current research found that the maximum dose that does not cause hyperalgesia in humans is 0.03 μg/kg (Petty et al., 1994-29). However, such low dose limits the application of NGF and also limits the expansion of its indications, such as use for the central nervous system.

Therefore, in order to avoid the above problems, it is necessary to seek a recombinant hNGF capable of alleviating side effects such as pain or even painlessness, thereby increasing the dosage and the subjects, and providing the possibility to expand the indications and apply to the central nervous system.

SUMMARY

An object of the present disclosure is to provide a series of nerve growth factor mutants, i.e., recombinant hNGFs, which are capable of alleviating side effects such as pain and are even painless, More preferably, provided is a series of nerve growth factor mutants, which have a high biological activity and are capable of alleviating side effects such as pain or even painless. To achieve the above object, the present disclosure adopts the following technical solutions.

Provided is a nerve growth factor mutant, in which mutation sites of the mutant include: Phe12Glu, Lys32Gly, Lys32Leu, Lys32Tyr, Arg59Leu, Arg59Ala, Asp65Ala, Asp65Gly, Lys74Leu, Lys88Phe Lys88Leu, Lys88Glu, Lys88Gly, Gln96Glu, Arg114Val, Arg114Phe, Arg114Gly, Arg114Leu, Phe101Ala, or any combination of the above mutation sites with respect to a parental nerve growth factor; preferably with respect to a parental human nerve growth factor; and preferably with respect to a parental wild-type human nerve growth factor.

The nerve growth factor mutant has an amino acid sequence of any one of SEQ ID No: 3 to SEQ ID No: 21 in the sequence listing.

Provided is a nucleotide sequence, encoding the nerve growth factor mutant.

The nucleotide sequence is a nucleotide sequence of SEQ ID No: 22 to SEQ ID No: 40 in the sequence listing.

The recombinant hNGF mutant of the present disclosure is obtained through single point mutation based on the wild-type hNGF sequence, and the amino acid sequences thereof and the corresponding nucleotide sequences encoding them are shown as follows:

Phe12Glu: having an amino acid sequence as shown in SEQ ID No: 3, encoded by a nucleotide sequence as shown in SEQ ID No: 22;

Lys32Gly: having an amino acid sequence as shown in SEQ ID No: 4, encoded by a nucleotide sequence as shown in SEQ ID No: 23;

Lys32Leu: having an amino acid sequence as shown in SEQ ID No: 5, encoded by a nucleotide sequence as shown in SEQ ID No: 24;

Lys32Tyr: having an amino acid sequence as shown in SEQ ID No: 6, encoded by a nucleotide sequence as shown in SEQ ID No: 25;

Arg59Leu: having an amino acid sequence as shown in SEQ ID No: 7, encoded by a nucleotide sequence as shown in SEQ ID No: 26;

Arg59Ala: having an amino acid sequence as shown in SEQ ID No: 8, encoded by a nucleotide sequence as shown in SEQ ID No: 27;

Asp65Ala: having an amino acid sequence as shown in SEQ ID No: 9, encoded by a nucleotide sequence as shown in SEQ ID No: 28;

Asp65Gly: having an amino acid sequence as shown in SEQ ID No: 10, encoded by a nucleotide sequence as shown in SEQ ID No: 29;

Lys74Leu: having an amino acid sequence as shown in SEQ ID No: 11, encoded by a nucleotide sequence as shown in SEQ ID No: 30;

Lys88Phe: having an amino acid sequence as shown in SEQ ID No: 12, encoded by a nucleotide sequence as shown in SEQ ID No: 31;

Lys88Leu: having an amino acid sequence as shown in SEQ ID No: 13, encoded by a nucleotide sequence as shown in SEQ ID No: 32;

Lys88Glu: having an amino acid sequence as shown in SEQ ID No: 14, encoded by a nucleotide sequence as shown in SEQ ID No: 33;

Lys88Gly: having an amino acid sequence as shown in SEQ ID No: 15, encoded by a nucleotide sequence as shown in SEQ ID No: 34;

Gln96Glu: having an amino acid sequence as shown in SEQ ID No: 16, encoded by a nucleotide sequence as shown in SEQ ID No: 35;

Arg114Val: having an amino acid sequence as shown in SEQ ID No: 17, encoded by a nucleotide sequence as shown in SEQ ID No: 36;

Arg114Phe: having an amino acid sequence as shown in SEQ ID No: 18, encoded by a nucleotide sequence as shown in SEQ ID No: 37;

Arg114Gly: having an amino acid sequence as shown in SEQ ID No: 19, encoded by a nucleotide sequence as shown in SEQ ID No: 38;

Arg114Leu: having an amino acid sequence as shown in SEQ ID No: 20, encoded by a nucleotide sequence as shown in SEQ ID No: 39; and Phe101Ala: having an amino acid sequence as shown in SEQ ID No: 21, encoded by a nucleotide sequence as shown in SEQ ID No: 40.

Provided is a long-acting nerve growth factor mutant, in which the long-acting nerve growth factor mutant is obtained from any one of the above amino acid sequences.

Preferably, the long-acting nerve growth factor mutant is obtained through chemical modification, and preferably, the long-acting nerve growth factor mutant is a conjugate of polyethylene glycol with a nerve growth factor mutant.

Preferably, the long-acting nerve growth factor mutant is a fusion protein obtained by fusing with an other protein. Preferably, the other protein is a human albumin, a human albumin analog, a fragment of a human albumin, an Fc moiety of an immunoglobulin, an analog of an Fc moiety of an immunoglobulin, or a fragment of an Fc moiety of an immunoglobulin.

Preferably, the fusion protein is obtained by fusing a C-terminal of the long-acting nerve growth factor mutant with an N-terminal of an albumin or an Fc protein directly or via a peptide linker.

Provided is an expression vector, including the nucleotide sequence.

The expression vector is selected from the group consisting of a DNA vector and a virus vector.

The DNA vector is selected from the group consisting of a DNA plasmid vector, a liposome bound thereto, a molecular conjugate bound thereto, and a polymer bound thereto, and preferably, the DNA plasmid vector is a eukaryotic expression vector; and the virus vector is selected from the group consisting of an adeno-associated virus vector, a lentivirus vector and an adenovirus vector.

Provided is a method for expressing the expression vector, including: transfecting the expression vector into a host cell, and culturing the resulting recombinant cell to express the expression vector, so as to obtain the nerve growth factor mutant.

Provided is a host cell, including the expression vector.

The host cell is a mammalian cell.

The mammalian cell is a Chinese hamster ovary cell, a human embryonic kidney 293 cell, a COS cell or a Hela cell.

Provided is a pharmaceutical composition, including a pharmaceutically acceptable excipient, and one or more of the above-mentioned nerve growth factor mutant, the above-mentioned expression vector, and the above-mentioned host cell.

The medicament of the present disclosure may be prepared into various forms such as an injection, a capsule, a tablet or powder, and medicaments having the above various dosage forms may be prepared according to a conventional method in the field of pharmacy.

The pharmaceutical composition is preferably an injection including a pharmaceutically acceptable excipient and the above-mentioned nerve growth factor mutant.

If necessary, one or more pharmaceutically acceptable carriers may be further added to the above pharmaceutical composition, and the carrier includes conventional diluents, stabilizers, surfactants, preservatives and the like in the pharmaceutical field.

Provided is use of the nerve growth factor mutant in the preparation of a medicament for treating a nervous system disease. The nervous system disease refers to a disease associated with neuronal degeneration or injury in the central and/or peripheral nervous system. Specific examples of the nervous system disease include, but are not limited to, Alzheimer's disease, Parkinson's disease, Huntington's disease, stroke, ALS, peripheral neuropathy, and other disorders characterized by necrosis or loss of neuron regardless central neuron, peripheral neuron, or motorneuron, except treating nerve damage caused by trauma, burns, kidney failure, or injury. For example, peripheral neuropathy associated with certain disorders is such as a neuropathy associated with diabetes, AIDS or chemotherapy.

The medicament for treating a nervous system disease prepared by a nerve growth factor mutant may be administered to a patient. The exact dosage will depend on the disease to be treated, and may be determined by one skilled in the art using known techniques. Additionally, as is known in the art, an adjustment needs to be made based on age, weight, general health, sex, diet, time of administration, drug interaction, and severity of the disease, and this may be determined by one skilled in the art through routine experimentation. The patient mentioned herein includes human, and other animals and organisms. Therefore, these methods may be used for treating human and livestock.

The administration of the medicament for treating a nervous system disease prepared by the nerve growth factor mutant of the present disclosure may be carried out by various methods, including, but not limited to, oral, subcutaneous, intravenous, intracerebral, intranasal, transdermal, intraperitoneal, intramuscular, intrapulmonary, vaginal, rectal, and intraocular administrations. Under some circumstances, such as treating a wound, it may be applied directly in a form of a solution or spray.

The pharmaceutical composition of the present disclosure includes the nerve growth factor mutant in a form suitable for administration to a patient. In a preferred example, the pharmaceutical composition is in a water soluble form, and may include, for example, a carrier, a excipient, a stabilizer, a buffer, a salt, an antioxidant, a hydrophilic polymer, an amino acid, a carbohydrate, an ionic or nonionic surfactant, polyethylene glycol, propylene glycol or the like. The medicament prepared by the nerve growth factor mutant may also be implanted in a sustained release form by techniques known in the art or embedded in a microcapsule form.

Provided is use of the nerve growth factor mutant in the preparation of a medicament for effectively reducing weight.

Provided is use of the nerve growth factor mutant in the preparation of a long-acting nerve growth factor.

Advantages of the present disclosure are shown as follows. As compared with the wild-type nerve growth factor in the prior art, the present disclosure may alleviate side effects such as pain and even be painless, and further, the biological activity of part of the nerve growth factor mutants may be significantly improved.

The present disclosure will be further described hereinafter in conjunction with drawings and specific embodiments, which are not intended to limit the scope of the present disclosure. All equivalent substitutions in the art in accordance with the present disclosure fall into the scope of the present disclosure.

DETAILED DESCRIPTION

Figure 1:
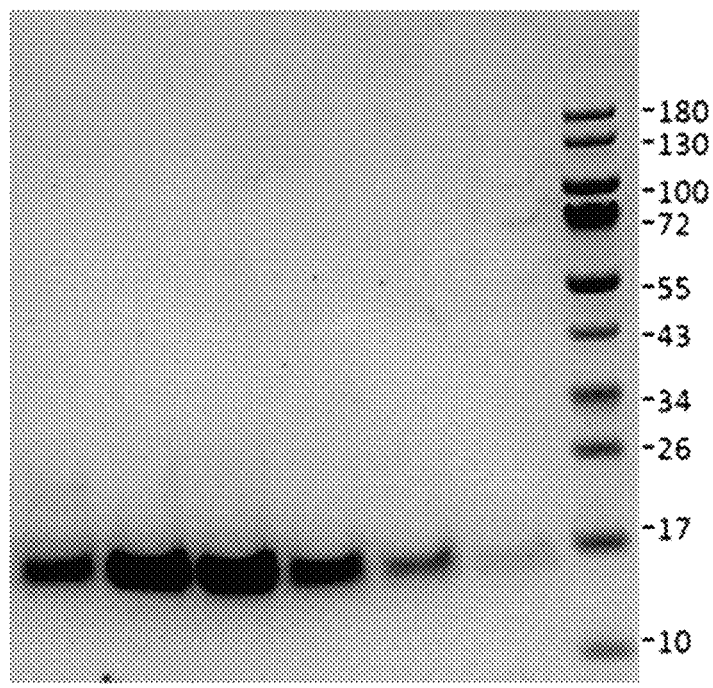
FIG. 1 is a result of the SDS PAGE electrophoresis of the wild-type hNGF purified by Superdex 75 column in Example 4.

Example 1: Plasmid Construction of Wild-Type hNGF and its Mutants

1. Construction of Expression Plasmid Containing DNA Sequence of Wild-Type hNGF

The DNA sequence of wild-type hNGF was synthesized (SEQ ID NO: 1 in the sequence listing), and the target sequence was amplified by PCR using primers (F: GGAATTCATGTCCATGTTG (SEQ ID NO: 41), R: CAAGCTTTCAGGCTCTTCT (SEQ ID NO: 42)). The PCR product was digested with EcorI (NEB #R0101S), and then the resulting digested product was subjected to a secondary digestion with Hind III (NEB #R0104S). The pcDNA3.1(-) expression vector was digested in the same manner. The digested vector and the fragments amplified by PCR were subjected to agarose gel electrophoresis. The target fragments were cleaved, and the digested vector and the target DNA fragments were respectively recovered by using a DNA gel recovery kit (TIANGEN, #DP209-03) and were ligated by a DNA ligase kit (Takara/6022) at 16° C. for 1 h, to complete the plasmid construction of the wild-type hNGF.

2. Construction of Expression Plasmid Containing DNA Sequence of hNGF Mutants

In the same manner as the above, the plasmids of all mutants were synthesized and constructed. The DNA sequences of the mutants were nucleotide sequences from SEQ ID No: 22 to SEQ ID No: 40 in the sequence listing.

Example 2: Transformation and Extraction of Plasmids Containing hNGF and its Mutants 1. Transformation The plasmids containing hNGF and its mutants constructed in the above Example 1 were subjected to a heat shock transformation. The top 10 competent cells (Tiangen/CB104-02) were taken out from the −70° C. refrigerator and immediately thawed on ice, and 50 µl of competent cells were taken for transformation. 2 µl of the plasmid was added to the 50 µl of competent cells, mixed by flicking, subjected to an ice bath for 30 min, and then subjected to a dry bath at 42° C. for 90 s, during which the centrifuge tube was not shaken, and the centrifuge tube was immediately placed on ice for 2 min after taking out of the dry bath. 500 µl of antibody-free LB (Luria-Bertani)/SOC (Super Optimal broth with Catabolite repression) medium was added, and cultured at 37° C. for 45 min on a shaker at 150 rpm/min. All the liquid in the centrifuge tube was poured onto the LB plate and spread evenly. The plate, after drying, was inverted in an incubator for 16 h.

2. Large Scale Extraction of Plasmid

The single colonies obtained in the above 2.1 experiment were picked up, inoculated into 500 µl of LB liquid medium and cultured at 37° C. for 7 h, and the bacterial solution was sent for sequencing. The correct bacterial solution confirmed by sequencing was subjected to a lot of shaking, and 500 µl of the bacterial solution was inoculated into 500 ml of LB medium and cultured at 37° C. for 16 h. The overnight cultured solution was collected by centrifugation at 4° C., centrifuged at 6000×g for 10 min and the supernatant was completely discarded. The plasmid was large-scale extracted by using a Plasmid Maxi Kit (purchased from QIAGEN, Cat. No. 12163), and the concentration was measured for use.

Example 3: Expression of Wild-Type hNGF and its Mutants

The wild-type hNGF and its mutants plasmids large-scale extracted in the above Example 2 were transfected into 293F cells, and the expression supernatant was collected and quantified on day 4 after transfection.

Experimental Procedures:

1. One day before transfection, 900 ml of 293F cells in total were inoculated at $0.5 \times 10^6$/ml in 300 ml/bottle.

2. Cells were counted on the day of the transfection, and the cell density was about $1.0 \times 10^6$/ml with a viability of 99% or more.

3. Transfection: 36 ml of a cell culture medium was taken into an 125 ml culture flask; 360 ug of plasmid was added and mixed evenly; and then 1080 ug of PEI was added and mix evenly, leave it to stand at room temperature for 15 min, mixed with cells at about 12.3 ml/bottle, and incubated at 37° C., in 8% $CO_2$, under 120 RPM.

4. On the fourth day after the transfection, the cell supernatant was collected and centrifuged at 10000 g for 20 min.

5. The supernatant was collected and filtered at 0.45 um, to obtain a protein supernatant of wild-type hNGF and its mutants.

6. SDS-PAGE detection, quantification by silver nitrate staining.

Example 4: Purification of Wild-Type hNGF and its Mutants

The protein supernatant of the NGF and its mutants obtained in the above Example 3 was purified.

1. Cation exchange chromatography: the protein supernatant of wild-type hNGF and its mutants was first adjusted to pH 4.0 with acetic acid and water. A CM Sepharose FF column was fully equilibrated with 0.05 mol/L acetate buffer (pH 4.0) and then loaded. After the loading was completed, it was rinsed with an equilibration solution to the baseline, and then impure peaks were eluted to the baseline with an equilibration solution of 0.05 mol/L Tris-HCl (pH 9.0), and finally subjected to a gradient elution with 0.05 mol/L Tris-HCl and 0.05 mol/L Tris-HCl-0.4 mol/L NaCl (pH 9.0). The target peak was collected according to the ultraviolet absorption, in which the collection was started when the number shown on the UV detector began to rise, and stopped when the number was lowered to the baseline.

2. Hydrophobic chromatography: a Butyl Sepharose 4 FF column was well equilibrated with 0.02 mol/L phosphate (pH 6.8)-1.5 mol/L sodium chloride buffer. Into the target peak solution collected in step 1, a sodium chloride solid was added, such that the final concentration of sodium chloride in the solution was 1.5 mol/L. After the sodium chloride was fully dissolved, the sample was loaded at a speed of 120 cm/h. After the loading was completed, it was rinsed with an equilibration solution to the baseline, and then the target peak was collected by elution with 0.02 mol/L phosphate (pH 6.8).

3. Gel exclusion chromatography: Superdex 75 prep grade chromatography column was fully equilibrated with 0.05 mol/L phosphate-0.15 mol/L sodium chloride buffer at pH 6.8. Then, the target peak collected in step 2 was loaded, in which the collection was started when the number shown on the UV detector began to rise from the baseline, and stopped when the number was lowered to the baseline.

The SDS PAGE of the wild-type hNGF purified by Superdex 75 column is shown in FIG. 1, indicating that the prepared NGF has high purity. The samples with target protein peaks of the collected wild-type hNGF and its mutants were concentrated to 0.4 mg/ml by using an ultrafiltration tube, and stored at 4° C. for subsequent experiments.

Example 5: Measurement for the Activity of Wild-Type hNGF and its Mutants by Chicken Embryo Method 1. Measurement for the Activity of Wild-Type hNGF and its Mutants Activity by Chicken Embryo Dorsal Root Ganglion Method The wild-type hNGF (amino acid sequence is shown in the sequence listing) and its mutants (amino acid sequences were shown in the sequence listing) samples obtained in the above Example 4 were diluted. A solution: 6 ng of the extracted wild-type hNGF and its mutants samples were dissolved by adding 1 ml of a serum-free DMEM medium. B solution: 50 µl of A solution was added with 4.95 ml of serum-free DMEM medium. C solution: 60 µl of B solution was added with 2.94 ml of serum-free DMEM (3 ml in total) to achieve a final concentration (3 AU/ml). A and B solutions were diluted in a centrifuge tube, and C solution was placed in a cell bottle. C solution was used as a No. 1 bottle, and was further diluted by a factor of 3 to No. 2, No. 3, No. 4, No. 5 and No. 6 solutions to be tested. Each solution to be tested was added into one culture bottle at 2 ml/bottle. At the same time, a serum-free DMEM culture medium was used as a blank control, and the standard product purchased from the National Institute of Food and Drug Control was used as a positive control (reference product). After an 8-day-old chicken embryo dorsal root ganglion was added, the culture bottle was placed in a saturated humidity incubator in a 5% $CO_2$ and at 37° C., and the results were observed after 24 h.

The content of NGF per ml of the sample to be tested when growing best is used as 1 activity unit (AU). The titer was calculated from end-point judgment, which was deemed as the best dilution for growing taken from the 3rd and 4th dilutions back counted from the dilution having the negative control result. The reference product is a standard product purchased from the National Institute of Food and Drug Control, in which the capacity of each is 1000 AU.

The formula for calculating the specific activity of NGF is shown as follow:

> specific activity of the sample to be tested (AU/mg)=activity of the reference product (AU/ml)×[pre-dilution factor of the sampler×activity at the dilution point of the corresponding reference product (AU/ml)/actual activity of the reference product (AU/ml)]

Figure 2A:
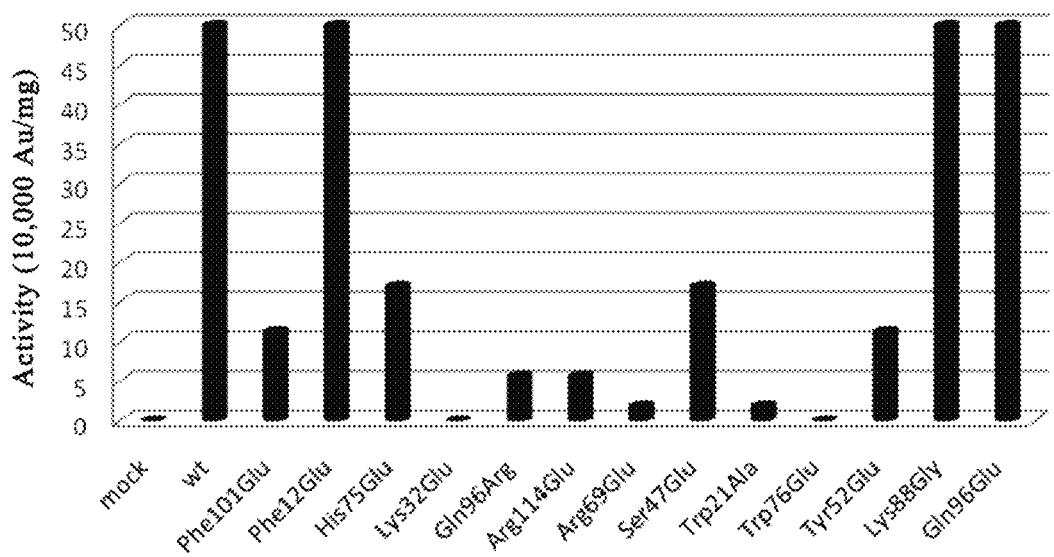
FIG. 2(A) and FIG. 2(B) are results of the activity measurement of the mutants in Example 5.
Figure 2B:
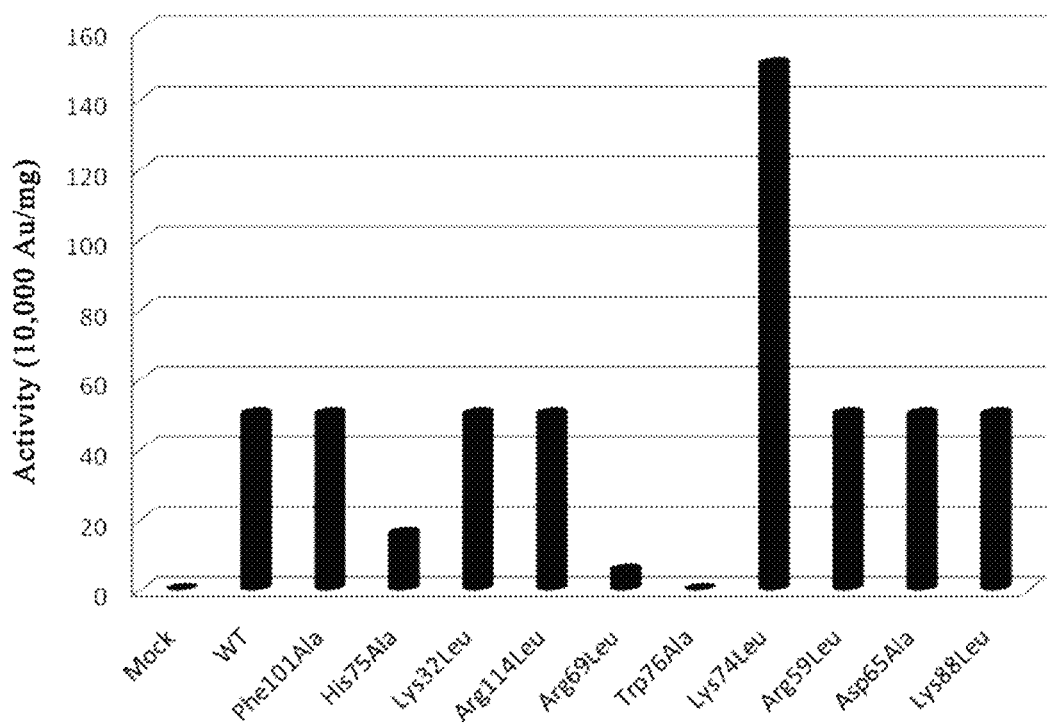

The results of the measurements are shown in FIGS. 2(A) and 2(B). The results showed that the hNGF mutants Phe12Glu, Lys32Leu, Arg59Leu, Asp65Ala, Lys74Leu, Lys88Leu, Lys88Gly, Gln96Glu, Phe101Ala, Arg114Leu all retained wild-type activity and even a higher activity.

Example 6: Measurement of the Activity of NGF and its Mutants by TF-1 Cell Method The detailed operation method was performed in accordance with the method in Example 1 of a patent entitled "Method for Quantitatively Measuring Nerve Growth Factor Activity" with a publication number of CN103376248A, and the test results of the specific activity were shown in the following table.

TABLE 1

| Sample Name | Specific Activity (U/mg) by Cell Method |
|---|---|
| Wild-type hNGF | 430,000 |
| Lys74Leu | 767,000 |
| Phe12Glu | 620,000 |
| Lys88Gly | 590,000 |
| Gln96Glu | 430,000 |

Example 7: Detection for Whether NGF and its Mutants Cause Pain (Pain Threshold)

Experimental principle: qualified mouse having a normal response to pain was screened, and injected a certain dose of NGF sample (wild-type or its mutants). The pain threshold of curved claw response in mouse by mechanical stimulation was determined, and subjected to a statistical analysis, and finally whether the sample caused mouse hyperalgesia was determined.

7-1. Observation of Short-Term Pain-Causing Condition

I. Experimental Material

Dynamic Plantar Aesthesiometer (Ugo Basile, Italy), model 37450.

II. Experiments

1. Screening of Qualified Mice

SPF grade CD-1 mice were ordered, in which the mice were male weighed 30-35 g.

By the Dynamic Plantar Aesthesiometer [Ugo Basile, Italy, model: 37450], the experimental animals were screened for qualified mice, in which the mean threshold of the left and right feet is between 7.5 and 10 and the P value for the threshold of the left and right feet in a same mouse is more than 0.05.

Mice were randomly divided into experimental groups and blank control groups, in which the experimental groups were divided into subgroups according to various samples and administration doses, and each group had 10 mice.

2. Design of Administration for NGF Samples 2.1. Screening of the Pain-Causing Dosage of Wild-Type Samples Drug formulation: a positive control NGF wild-type samples and each mutant sample were diluted by using sample stock solutions (50 mM PB, 150 mM NaCl, pH 6.8).

Blank control: stock solution of NGF samples.

Mode of administration and dosage: 20 μl were administered plantar subcutaneously to the left and right feet of mice respectively.

The minimum dose for a short-term administration was 1.25 μg per mouse, while the corresponding higher dose was administered to determine the ability to cause pain, see the dose labeled in FIG. 3 (B).

3. Measurement of Pain Threshold

Mechanical threshold measurements were performed at 1 h and 2 h after administration respectively, and values were recorded for observing the short-term administration (within 2 h).

4. Statistical Analysis for the Results

GraphPad Prism software was used for graph drawing and statistical analysis for the results. The difference in the mechanical thresholds between each dose group and the control group were compared, and the ability to cause pain of wild-type samples and mutants samples were analyzed.

Figure 3A:
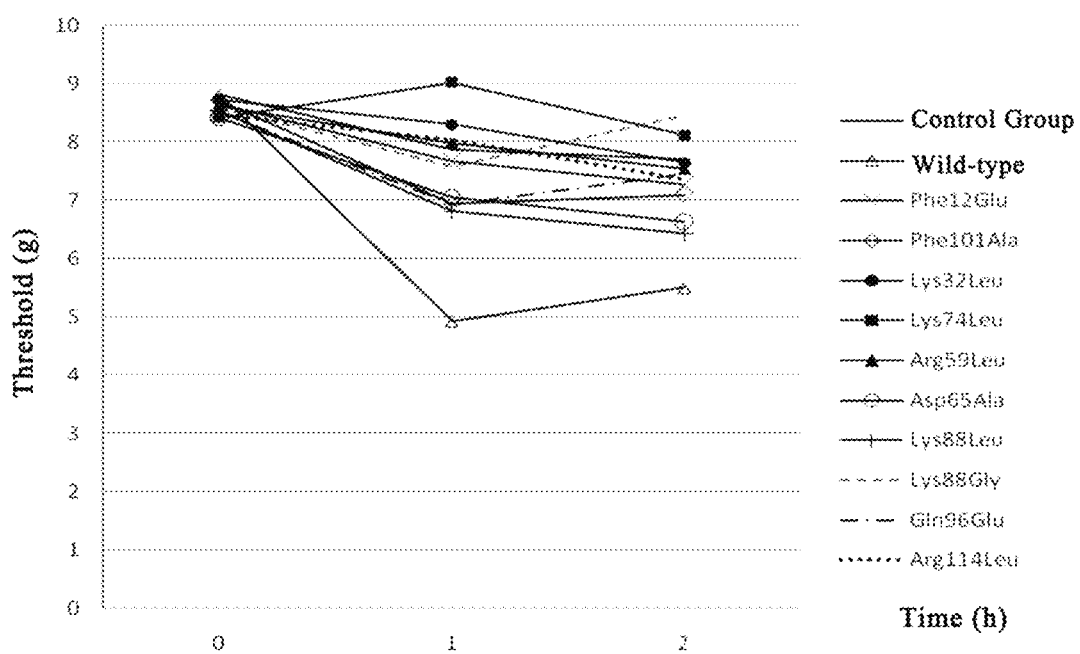
FIG. 3 (A) and FIG. 3 (B) are results of the pain threshold measurement of the short-term administrated to mice in Example 7.
Figure 3B:
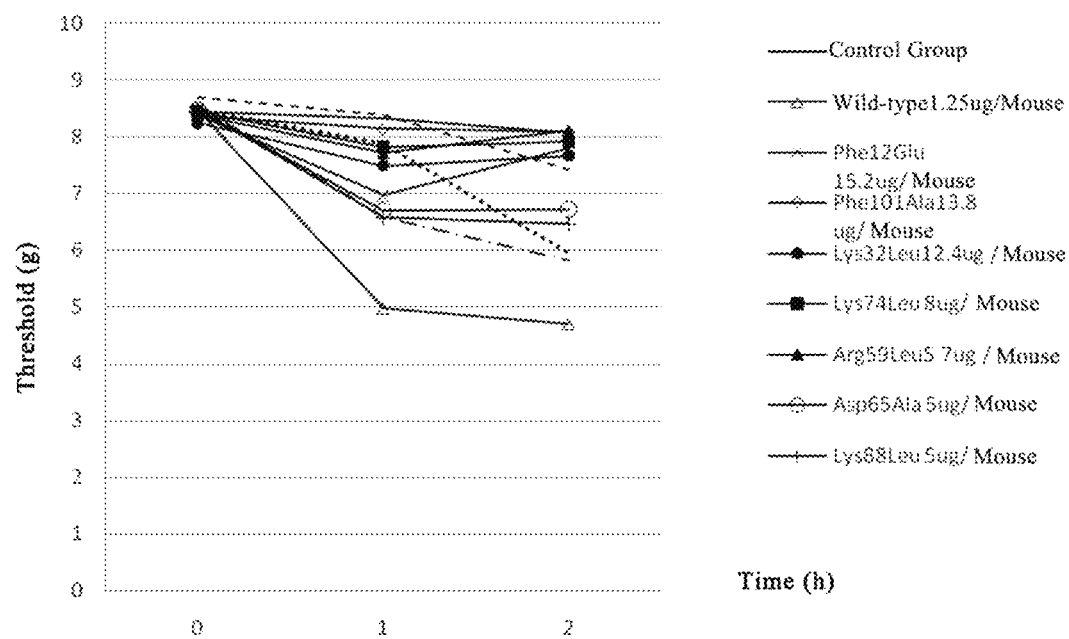

As can be seen from FIG. 3(A), when the minimum dose of administration was 1.25 μg per mouse, the control group had no pain, while the wild-type positive control group had a pain threshold of obviously less than 5 at 1 h, and the pain was obvious; the pain threshold for each mutant experimental group was about 7, and there was no significant difference as compared with the negative control group, indicating that the short-term injection of mutants were basically no painful;

As can be seen from FIG. 3(B), when the administration dose of the control group and the wild-type was 1.25 μg per mouse and the administration dose of the experimental group was increased, the control group had no pain, while the wild-type positive control group had a pain threshold of obviously less than 5 at 1 h, and the pain was obvious; the pain threshold for each mutant experimental group was about 7, and there was no significant difference as compared with the negative control group, indicating that the short-term injection of mutants were also basically no painful in the case of increasing the administration dose.

7-2. Observation of Long-Term Pain-Causing Condition

Three of the above mutants No. 1 (Phe12Glu), No. 2 (Lys88Gly) and No. 3 (Arg114Leu) were randomly selected for long-term pain-causing test. Except that the three doses for this experiment were: 0.2 μg per mouse, 0.5 μg per mouse and 1.25 μg per mouse, once a day for 3 weeks, during which the pain threshold was measured continuously, the rest all were performed according to the method in 7-1 "observation of short-term pain-causing condition".

Figure 4A:
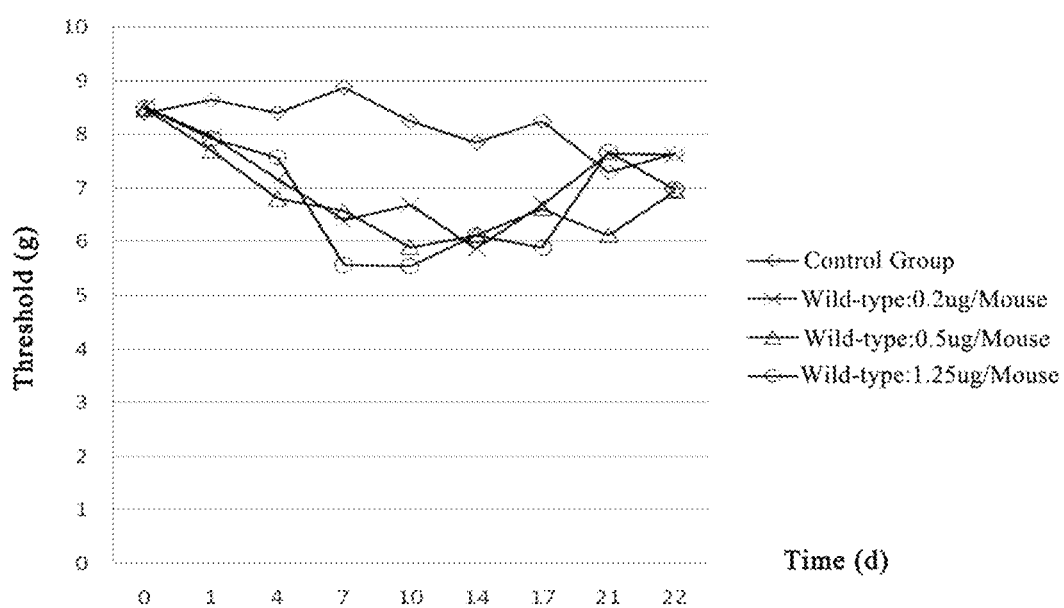
FIG. 4 (A), FIG. 4 (B) and FIG. 4 (C) are results of the pain threshold measurement of the long-term administrated to mice in Example 7.
Figure 4B:
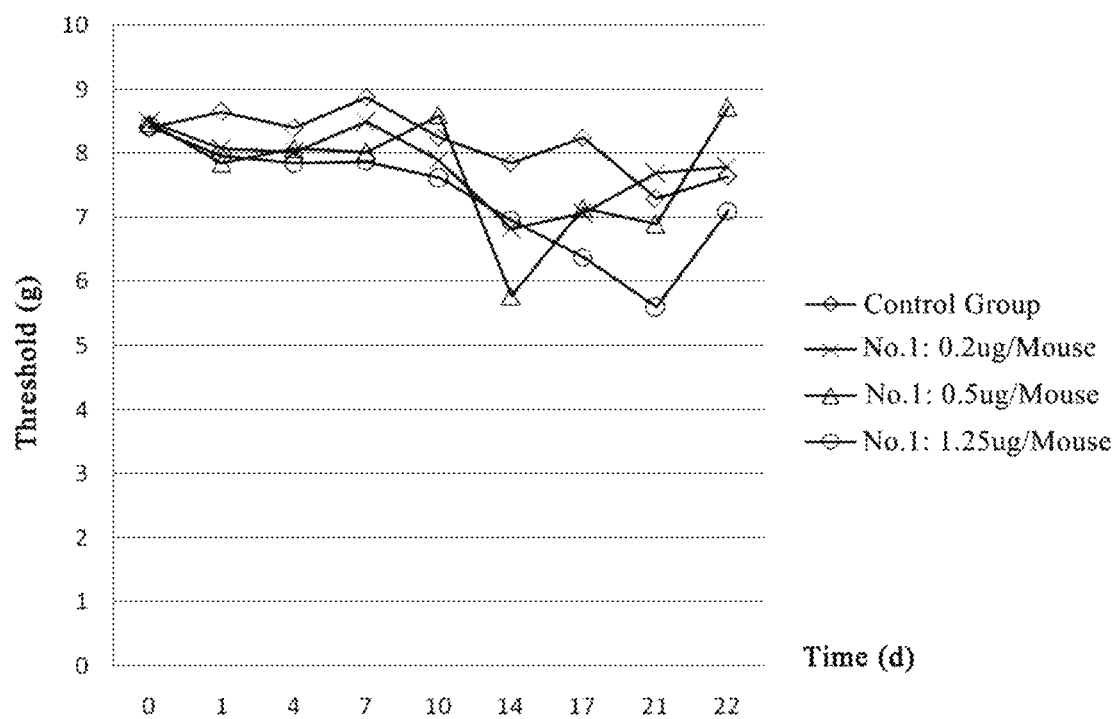
Figure 4C:
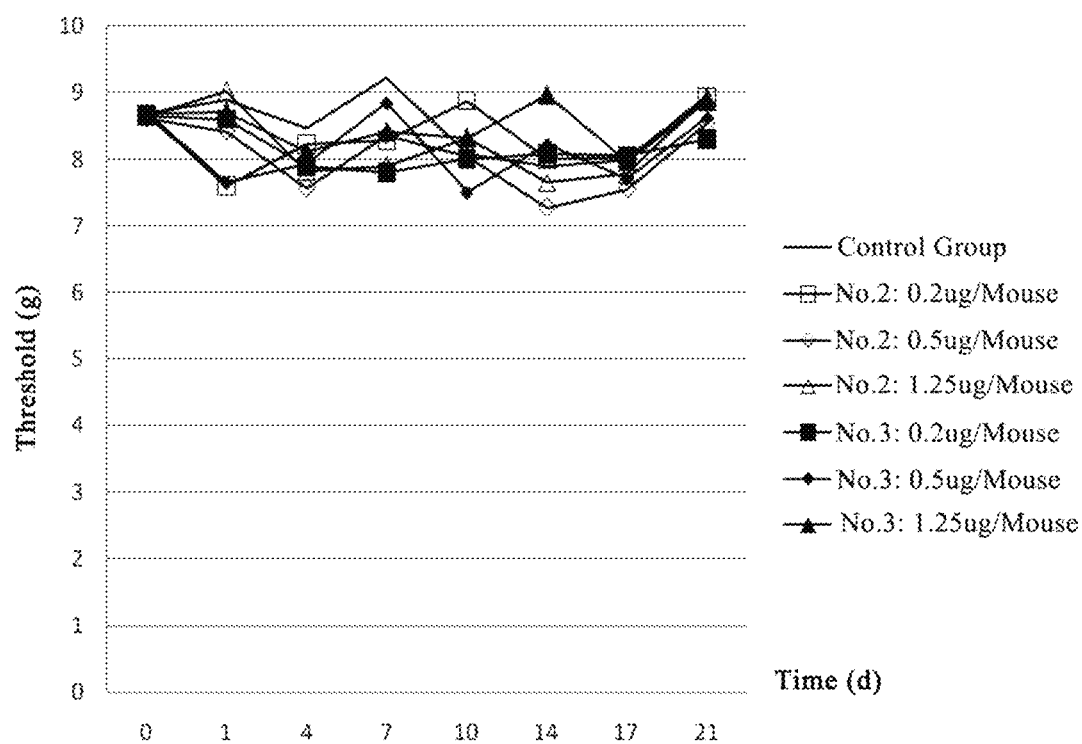

The results are shown in FIGS. 4(A), 4(B) and 4(C), indicating that as for the mutant Phe12Glu, the pain threshold was not significantly reduced within 14 days, and no pain was observed, while only a short-term pain was observed for a medium dose (0.5 μg per mouse) after 14 days; as for the mutant Lys88Gly and the mutant Arg114Leu, no obvious pain threshold change was showed during the test; and as for the wild-type NGF, the pain thresholds of three doses were reduced within 17 days gradually, and pain gradually appeared. In view of this, the mutants of the present disclosure have a significant pain reducing effect over the wild-type.

Example 8. Behavioral Test of Whether Wild-Type hNGF and its Mutants Cause Pain

The wild-type hNGF and its mutants samples were administered in the joints of the mice, and whether the samples cause pain were examined by leg lifting maintenance time and number of the mice according to behavior.

Experiments

1. Ordering of Mouse

SPF grade CD-1 mice were ordered, in which the mice were male weighed 30-35 g. They were randomly divided into experimental groups, blank control groups (abbreviated as control groups) and positive control groups, in which each group was divided into seven subgroups according to the dose, and each group was randomly selected for 6 mice.

2. Administration Dose and Time 2.1. Administration Dose

Positive control: the wild-type hNGF was diluted with a sample stock solution (50 mM PB, 150 mM NaCl, pH 6.8) to 1.25 μg/10 μl group;

Experimental group: the preparation method of the mutant drug was the same as the positive control, and the mutants Phe12Glu, Lys88Gly and Arg114Leu were diluted to 1.25 μg/10 μl group and 0.5 μg/10 μl group;

Blank control: normal saline.

2.2. Mode of Administration

Drugs were injected into the joint in hind legs of the mice, in which 10 μl was administered into each joint cavity.

2.3. Time of Administration

Each dose group was administered in a single continuous 3-4 days. That is, the administration was performed at 10 am on the first day, and at the same time points on the 2nd, 3rd, and 4th days thereafter.

3. Behavioral Observation

Observation was performed at 2nd and 4th hours after the administration of each experimental group, and at the same time points on the 2nd, 3rd, and 4th days of administration.

Observation indicators: the numbers of the mouse spontaneous leg lifting within 2 min and the maintenance time (s) of each leg lifting were used to calculate the accumulated time of leg lifting.

4. Statistical Analysis for the Results

A two-way ANOVA of GraphPad Prism software was used to compare the leg lifting maintenance time, and analyze whether different samples cause pain.

Figure 5:
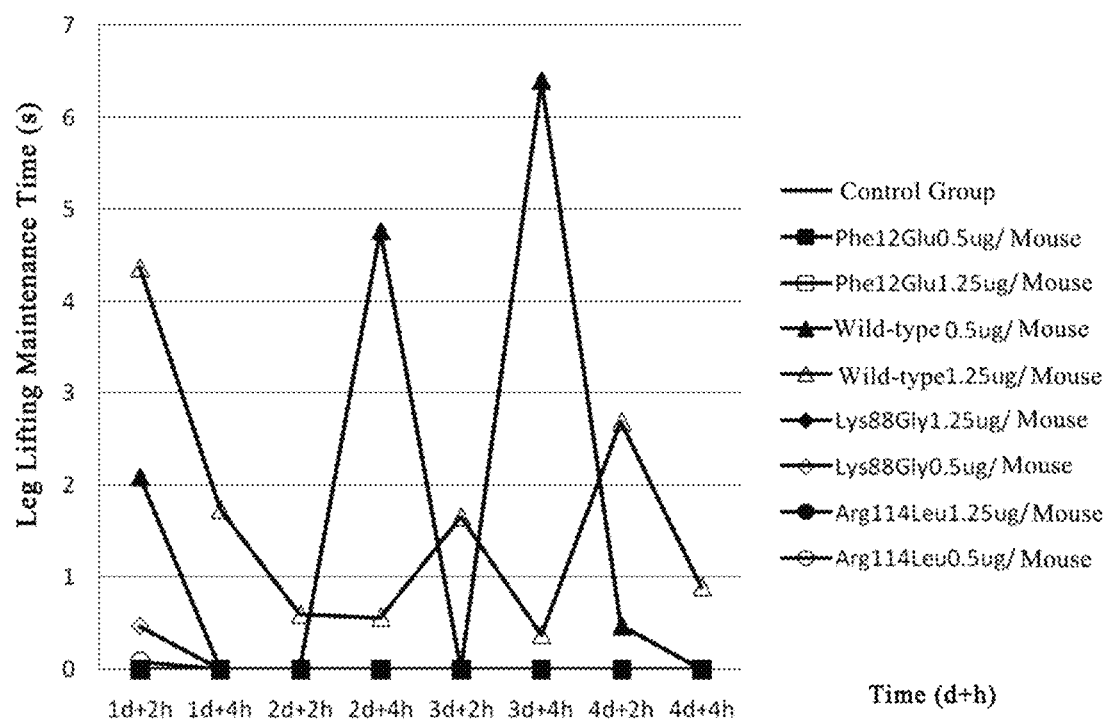
FIG. 5 is a result of the behavioral experiments of the mice injected with a mutant and a wild-type hNGF respectively in Example 8 by observing the leg lifting maintenance time.

The experimental results are shown in FIG. 5. The wild-type hNGF group may cause obvious pain at each time point after the injection of the drug. There is no leg-lifting behavior or pain abnormality in the continuous administration of each dose group of the mutant, thereby determining that the mutants did not cause pain. Chi-square analysis showed that there was a significant difference between the positive control group and the experimental group at each detection time point.

What is claimed is:

1. A nerve growth factor mutant comprising Phe12Glu with reference to the amino acid positions set forth in a wild-type human nerve growth factor provided by SEQ. ID. NO: 2.

2. The nerve growth factor mutant according to claim 1, further comprising a chemical modification.

3. The nerve growth factor mutant according to claim 2, wherein the chemical modification is PEGylation.

4. The nerve growth factor mutant according to claim 1, wherein the nerve growth factor mutant is fused to a protein.

5. The nerve growth factor mutant according to claim 4, wherein the protein is a human albumin, a fragment of a human albumin, an Fc moiety of an immunoglobulin, or a fragment of an Fc moiety of an immunoglobulin.

6. The nerve growth factor mutant according to claim 4, wherein the nerve growth factor mutant is fused to the protein by fusing a C-terminal of the nerve growth factor mutant with a N-terminal of an albumin or an Fc protein directly or via a peptide linker.

7. A pharmaceutical composition, comprising a pharmaceutically acceptable excipient, and the nerve growth factor mutant of claim 1.

8. The pharmaceutical composition according to claim 7, wherein the pharmaceutical composition is formulated for injection.

9. The nerve growth factor mutant according to claim 1, wherein the nerve growth factor mutant comprising Phe12Glu has an amino acid sequence of SEQ ID No: 3.

* * * * *